US012678045B2

(12) United States Patent
Deeds et al.

(10) Patent No.: US 12,678,045 B2
(45) Date of Patent: Jul. 14, 2026

(54) SYSTEM FOR ASSOCIATING DEVICE DATA

(71) Applicant: Stryker Corporation, Kalamazoo, MI (US)

(72) Inventors: Thomas Deeds, Seattle, WA (US); Krishna Sandeep Bhimavarapu, Kalamazoo, MI (US); Madhu Thomas, London (CA); Celso Henrique Farnese Pires Pereira, Portage, MI (US); Jerald A. Trepanier, Augusta, MI (US); Kirby M. Neihouser, Portage, MI (US); Madhu Sandeep Thota, Portage, MI (US)

(73) Assignee: Stryker Corporation, Portage, MI (US)

( * ) Notice: Subject to any disclaimer, the term of this patent is extended or adjusted under 35 U.S.C. 154(b) by 307 days.

(21) Appl. No.: 18/561,422

(22) PCT Filed: May 26, 2022

(86) PCT No.: PCT/US2022/031012
§ 371 (c)(1),
(2) Date: Nov. 16, 2023

(87) PCT Pub. No.: WO2022/251412
PCT Pub. Date: Dec. 1, 2022

(65) Prior Publication Data
US 2024/0268668 A1 Aug. 15, 2024

Related U.S. Application Data

(60) Provisional application No. 63/193,777, filed on May 27, 2021.

(51) Int. Cl.
*A61B 5/00* (2006.01)

(52) U.S. Cl.
CPC ............ *A61B 5/002* (2013.01); *A61B 5/6891* (2013.01); *A61B 5/7435* (2013.01); *A61B 5/7465* (2013.01); *A61B 2560/0214* (2013.01)

(58) Field of Classification Search
CPC ....... H04W 4/02; H04W 4/024; H04W 4/029; H04W 4/90; H04W 64/00; H04W 76/50;
(Continued)

(56) References Cited

U.S. PATENT DOCUMENTS 7,242,306 B2 7/2007 Wildman et al.
7,570,152 B2 8/2009 Smith et al.
(Continued)

FOREIGN PATENT DOCUMENTS

WO 2017/151683 A1 9/2017
WO 2020/264140 A1 12/2020
(Continued)

*Primary Examiner* — Lana N Le
(74) *Attorney, Agent, or Firm* — Gardner, Linn, Burkhart & Ondersma LLP

(57) ABSTRACT

A patient support apparatus for supporting a patient includes a plurality of pseudo-anchors that are used to determine relative position estimates with respect to an anchor affixed at a known location to a wall of a healthcare facility. From these position estimates and the knowledge of the location of the pseudo-anchors on the body of the patient support apparatus, the position and/or orientation of the patient support apparatus is determined. The pseudo-anchors may also determine the relative location of a mobile medical device with respect to the patient support apparatus. If the medical device is closely positioned to the patient support apparatus, the patient support apparatus associates the medical device with the patient support apparatus and transmits data to a server indicating the association. The medical device may include a location module and a data collection
(Continued)

module that transmit information to the patient support apparatus for forwarding to the server.

20 Claims, 16 Drawing Sheets

(58) Field of Classification Search
CPC ... H04M 11/04; H04M 2242/04; A61B 5/002; A61B 5/6891; A61B 5/7435; A61B 5/7465; A61B 2560/0214; A61B 2505/03; A61B 2560/0443; A61B 2562/0204; A61B 2562/0252; A61B 5/1115; A61B 5/1117
See application file for complete search history.

(56) References Cited

U.S. PATENT DOCUMENTS

| | | | |
|---|---|---|---|
| 8,334,777 B2 | 12/2012 | Wilson et al. | |
| 8,334,779 B2 | 12/2012 | Zerhusen et al. | |
| 8,552,903 B2 | 10/2013 | Julian et al. | |
| 8,756,078 B2 | 6/2014 | Collins, Jr. et al. | |
| 8,786,402 B2 | 7/2014 | Barnes | |
| 9,320,662 B2 | 4/2016 | Hayes et al. | |
| 9,427,365 B2 | 8/2016 | Richards et al. | |
| 9,554,286 B2 | 1/2017 | Ghabra et al. | |
| 9,569,591 B2 | 2/2017 | Vanderpohl, III | |
| 9,571,985 B2 | 2/2017 | Borrazzi et al. | |
| 9,788,151 B2 | 10/2017 | Duan et al. | |
| 10,064,012 B1 | 8/2018 | Boston et al. | |
| 10,258,538 B2 | 4/2019 | Barta et al. | |
| 10,474,808 B2 | 11/2019 | Huster | |
| 10,486,646 B2 | 11/2019 | Ledvina et al. | |
| 10,608,699 B2 | 3/2020 | Nabki et al. | |
| 10,759,389 B2 | 9/2020 | Ledvina et al. | |
| 10,811,136 B2 | 10/2020 | Bhimavarapu et al. | |
| 10,846,961 B2 | 11/2020 | de Perthuis et al. | |
| 10,893,988 B2 * | 1/2021 | Tessmer | A61B 5/689 |
| 11,019,195 B2 | 5/2021 | Ledvina et al. | |
| 11,026,607 B2 | 6/2021 | Martin et al. | |
| 11,082,809 B1 | 8/2021 | Burowski et al. | |
| 11,153,810 B2 | 10/2021 | Yoon et al. | |
| 11,289,194 B1 | 3/2022 | Pipher et al. | |
| 11,301,651 B2 | 4/2022 | Studerus et al. | |
| 11,343,645 B2 | 5/2022 | Yoon et al. | |
| 11,400,889 B2 | 8/2022 | Parthasarathi et al. | |
| 11,610,671 B2 | 3/2023 | Hochworter | |
| 11,638,233 B2 | 4/2023 | Shin et al. | |
| 2006/0183426 A1 * | 8/2006 | Graves | H04W 4/029 |
| | | | 455/63.1 |
| 2008/0312971 A2 | 12/2008 | Rowsow et al. | |
| 2011/0208541 A1 | 8/2011 | Wilson et al. | |
| 2014/0297327 A1 | 10/2014 | Heil et al. | |
| 2014/0320290 A1 | 10/2014 | Reeder et al. | |
| 2016/0140307 A1 | 5/2016 | Brosnan et al. | |
| 2017/0287316 A1 | 10/2017 | Wildman et al. | |
| 2017/0340498 A1 | 11/2017 | Tessmer et al. | |
| 2018/0028824 A1 | 2/2018 | Pivonka et al. | |
| 2018/0082573 A1 * | 3/2018 | Zuckerman | H04W 76/50 |
| 2020/0374682 A1 * | 11/2020 | Newman | H04W 4/90 |
| 2021/0014677 A1 | 1/2021 | Han et al. | |
| 2021/0065885 A1 | 3/2021 | Receveur et al. | |
| 2021/0160651 A1 * | 5/2021 | Lau | H04W 64/00 |
| 2021/0266710 A1 | 8/2021 | Martin et al. | |
| 2021/0360366 A1 | 11/2021 | Bailey et al. | |
| 2021/0400439 A1 | 12/2021 | Troester et al. | |
| 2022/0053292 A1 | 2/2022 | Hoff et al. | |
| 2022/0137204 A1 | 5/2022 | Nguyen et al. | |
| 2022/0139133 A1 | 5/2022 | Schober et al. | |
| 2022/0208372 A1 | 6/2022 | Bodurka et al. | |
| 2022/0241124 A1 | 8/2022 | Bhimavarapu et al. | |
| 2022/0287897 A1 | 9/2022 | Bhimavarapu et al. | |
| 2023/0188940 A1 * | 6/2023 | Andre | H04W 4/029 |
| 2023/0337941 A1 | 10/2023 | Pereira et al. | |
| 2024/0188906 A1 * | 6/2024 | Seoane | A61B 5/002 |
| 2025/0220835 A1 * | 7/2025 | Shum | H04W 4/029 |

FOREIGN PATENT DOCUMENTS

| WO | 2021/228946 A1 | 11/2021 |
|---|---|---|
| WO | 2021/236649 A1 | 11/2021 |
| WO | 2022/086515 A1 | 4/2022 |

* cited by examiner

SYSTEM FOR ASSOCIATING DEVICE DATA

This application claims priority to U.S. provisional patent application Ser. No. 63/193,777 filed May 27, 2021, by inventors Thomas Deeds et al. and entitled SYSTEM FOR ASSOCIATING MEDICAL DEVICE DATA, the complete disclosure of which is incorporated herein by reference.

BACKGROUND

The present disclosure relates to patient support apparatuses, such as beds, cots, stretchers, recliners, or the like. More specifically, the present disclosure relates to devices that are used in the care and/or treatment of patients while the patient is assigned to such a patient support apparatus.

Many devices, such as medical devices, are often used with a patient while the patient is positioned on a patient support apparatus. Such devices typically generate data regarding the patient that may be desirably forwarded to an electronic medical records (EMR) server and/or to one or more remote computing devices that display the data to remotely positioned caregivers. In order for this data to be meaningfully processed by either the EMR server and/or the remotely positioned caregivers, it must be associated with a particular patient, room, bed bay, caregiver, and/or other entity so that the data can be distinguished from other medical data. Often, such association requires one or more manual steps executed by a caregiver. In some cases, patient identity information is input into the device itself, and this identity information is transmitted with other data from the device to the EMR and/or remote computing device. This method requires that the transmitted patient data be properly secured against unauthorized disclosure so that unauthorized individuals do not gain access to the patient identity and his or her data. In other cases, an authorized individual may have to take manual steps to pair a radio onboard the device with a specific radio that is spaced away from the medical device.

SUMMARY

According to various embodiments, the present disclosure is directed to a system that overcomes past issues with associating data from medical devices and/or other types of devices, with the correct patient and/or with a correct proxy for the patient (e.g. the patient support apparatus to which the patient is assigned, the room and/or room bay to which the patient is assigned, etc.). That is, the present disclosure provides a system and method for automatically associating a device with the patient (or a proxy for the patient) if the device is positioned within a predetermined volume of space that surrounds all, or a portion of, the patient support apparatus. The automatic association allows data generated from the device to be properly categorized and, in some cases, stored in the correct electronic medical record for a particular patient. Alternatively, or additionally, this automatic association allows the data generated from the device to be associated with the patient, the patient's room (and/or another entity) so that remotely positioned caregivers can view the data on one or more remotely positioned electronic devices (e.g. smart phones), thereby allowing the caregivers to view such device data for a particular patient without requiring the caregivers to be present in the same room as the patient. Such automatic association avoids the need for an authorized user to manually associate the device with a specific patient.

According to a first aspect of the present disclosure, a patient support apparatus is provided that includes a support surface, first and second pseudo-anchors, a memory, and a controller. The first pseudo-anchor is coupled to a first location on the patient support apparatus and is adapted to wirelessly communicate with a mobile device in order to determine a first relative position of the mobile device with respect to the first pseudo-anchor. The second pseudo-anchor is coupled to a second location on the patient support apparatus and is adapted to wirelessly communicate with the mobile device in order to determine a second relative position of the mobile device with respect to the second pseudo-anchor. The memory contains pseudo-anchor location data identifying where the first and second locations are defined on the patient support apparatus. The controller is adapted to determine if the mobile device is positioned within a particular volume of space based on the first and second relative positions and the pseudo-anchor location data.

According to another aspect of the present disclosure, the patient support apparatus may further comprise a microphone adapted to convert sound from a patient positioned on the patient support apparatus into audio signals, and a wireless transceiver adapted to forward the audio signals to a headwall unit in which the anchor is housed. The headwall unit may then forward the audio signals to a nurse call system coupled to the headwall unit.

In some embodiments, the first pseudo-anchor is further adapted to wirelessly communicate with an anchor affixed at a known location to a wall of a healthcare facility, and to receive a third relative position of the mobile device with respect to the anchor.

In some embodiments, the controller is further adapted to use the third relative position to determine if the mobile device is inside or outside of a volume of space.

The patient support apparatus, in some embodiments, further comprises a network transceiver adapted to communicate with a computer network of a healthcare facility in which the patient support apparatus is positioned.

The controller, in some embodiments, is further adapted to forward data received from the mobile device to the computer network if the mobile device is positioned within the volume of space, and to not forward data received from the mobile device to the computer network if the mobile device is positioned outside of the volume of space.

The memory, in some embodiments, further includes a unique patient support apparatus identifier, and the controller is further adapted to forward the unique patient support apparatus identifier with the data received from the mobile device to the computer network when the mobile device is positioned within the volume of space.

In some embodiments, the controller is further adapted to forward a message to a server on the computer network indicating that the mobile device is positioned inside of the volume of space.

The controller, in some embodiments, is further adapted to forward a message to the server on the computer network indicating that the mobile device has moved outside of the volume of space.

In some embodiments, the controller is further adapted to receive from the anchor a fifth relative position of the device with respect to the anchor, and the controller is further adapted to use the fifth relative position to determine if the mobile device is inside or outside of the volume of space.

The first pseudo-anchor, in some embodiments, is adapted to repetitively update the third relative position. In such embodiments, the second pseudo-anchor is also adapted to repetitively update the fourth relative position, and the controller is further adapted to repetitively determine if the device is inside or outside of the volume of space based on the repetitively updated third and fourth relative positions.

In some embodiments, the controller is further adapted to forward patient support apparatus data to a server on the computer network as well as device data received from the mobile device when the mobile device is positioned within the volume of space.

The first and second pseudo-anchors, in some embodiments, are adapted to communicate with a tag coupled to the mobile device. The tag includes a location sensing module adapted to communicate location information to the first and second pseudo-anchors, and a data gathering module adapted to communicate data regarding the operation of the device to at least one of the first or second pseudo-anchors.

In some embodiments, the tag includes a common battery adapted to provide electricity to both the location sensing module and the data sensing module.

In some embodiments, the first and second pseudo-anchors are adapted to use ultra-wideband signals to determine the first and second relative positions. Alternatively, or additionally, the first and second pseudo-anchors may be adapted to use Bluetooth Low Energy (LE) signals to determine the first and second relative positions.

According to another embodiment of the present disclosure, a system is provided that includes an anchor, a patient support apparatus, and a server. The anchor is affixed at a known location to a wall of a healthcare facility. The patient support apparatus includes a support surface, first and second pseudo-anchors, a memory, a network transceiver, and a controller. The first pseudo-anchor is coupled to a first location on the patient support apparatus and is adapted to wirelessly communicate with the anchor in order to determine a first relative position of the first pseudo-anchor with respect to the anchor. The second pseudo-anchor is coupled to a second location on the patient support apparatus and is adapted to wirelessly communicate with the anchor in order to determine a second relative position of the second pseudo-anchor with respect to the anchor. The memory contains pseudo-anchor location data identifying where the first and second locations are defined on the patient support apparatus. The network transceiver is adapted to communicate with a computer network of a healthcare facility in which the patient support apparatus is positioned. The controller is adapted to use the first and second pseudo-anchors to determine a third relative position of a mobile device with respect to the patient support apparatus. The server is hosted on the computer network and adapted to communicate with a display. The server is further adapted to forward to the display both first data regarding a status of the patient support apparatus and second data regarding the mobile device.

According to another aspect of the present disclosure, the controller may further be adapted to forward the first and second data via the network transceiver to the server, and the display includes a network interface adapted to communicate with the server.

In some embodiments, the display is part of at least one of the following: a smart phone, a computer tablet, or a laptop computer.

The network transceiver, in some embodiments, is a first WiFi transceiver and the network interface is a second WiFi transceiver.

The controller, in some embodiments, is further adapted to use the anchor to determine the third relative position of the mobile device with respect to the patient support apparatus.

In some embodiments, the controller is further adapted to determine if the mobile device is inside or outside of a volume of space, and to send a message to the server indicating whether the mobile device is inside or outside of the volume of space.

The controller is further adapted, in some embodiments, to forward the following to the server via the network transceiver: (1) a first unique identifier associated with the patient support apparatus; (2) a second unique identifier associated with the anchor; and (3) a third unique identifier associated with the mobile device.

The server, in some embodiments, is adapted to determine a room number of a room within the healthcare facility in which the patient support apparatus is located based on the second unique identifier. The server, in some embodiments, is further configured to instruct the display to display the room number along with the first data and the second data.

In some embodiments, the first data includes at least one of the following items: a status of a brake onboard the patient support apparatus; a status of an exit detection system onboard the patient support apparatus; a status of a siderail onboard the patient support apparatus; height information of an adjustable height litter frame of the patient support apparatus; an occupancy status of the patient with respect to the patient support apparatus; or a status of a monitoring system onboard the patient support apparatus adapted to monitor a plurality of conditions of the patient support apparatus.

In some embodiments, the second data includes at least one of the following items: a battery status of the mobile device; a usage metric of the mobile device; a type of device the mobile device is; whether the mobile device is inside or outside of the volume of space; or a time at which the mobile device entered or exited the volume of space.

The controller, in some embodiments, is further adapted to repetitively update the third relative position of the mobile device with respect to the patient support apparatus and to repetitively determine if the device is inside or outside of the volume of space based on the repetitively updated third relative position.

The first and second pseudo-anchors, in some embodiments, are adapted to communicate with a tag coupled to the mobile device. The tag includes a location sensing module adapted to communicate location information to the first and second pseudo-anchors, and a data gathering module adapted to communicate data regarding the operation of the device to at least one of the first or second pseudo-anchors.

The tag, in some embodiments, includes a common battery adapted to provide electricity to both the location sensing module and the data sensing module.

The controller, in some embodiments, is further adapted to determine an orientation of the patient support apparatus relative to the wall based on the first and second relative positions and the pseudo-anchor location data.

According to another aspect of the present disclosure, a system is provided that includes a patient support apparatus and a tag. The patient support apparatus includes a support surface, first and second pseudo-anchors, a memory, a network transceiver, and a controller. The first pseudo-anchor is coupled to a first location on the patient support apparatus. The second pseudo-anchor coupled to a second location on the patient support apparatus. The memory contains pseudo-anchor location data identifying where the first and second locations are defined on the patient support apparatus. The network transceiver is adapted to communicate with a computer network of a healthcare facility in which the patient support apparatus is positioned. The controller is adapted to use the first and second pseudo-anchors to determine a first relative position of a mobile device with respect to the patient support apparatus. The tag is coupled to the mobile device and includes a location sensing module and a data gathering module. The location sensing module is adapted to communicate location information to the first and second pseudo-anchors, and the data gathering module is adapted to communicate data regarding the operation of the device to at least one of the first or second pseudo-anchors.

According to other aspects of the present disclosure, the tag may include a common battery adapted to provide electricity to both the location sensing module and the data sensing module.

In some embodiments, the system further includes a server hosted on the computer network that is adapted to communicate with a display. The server is further adapted to forward to the display both first data regarding a status of the patient support apparatus and second data regarding the mobile device.

In some embodiments, the controller is further adapted to forward the first and second data via the network transceiver to the server, and the display includes a network interface adapted to communicate with the server.

In some embodiments, the display is part of at least one of the following: a smart phone, a computer tablet, or a laptop computer.

The tag, in some embodiments, is further adapted to automatically start communicating with the first and second pseudo-anchors in response to a manually initiated triggering action.

The controller, in some embodiments, is further adapted to determine if the mobile device is inside or outside of a volume of space, and to send a message to the server indicating whether the mobile device is inside or outside of the volume of space.

The system, in some embodiments, further comprises an anchor affixed at a known location to a wall of a healthcare facility. The anchor is configured to wirelessly communicate with the first and second pseudo-anchors in order to determine relative positions of the first and second pseudo-anchors with respect to the anchor.

The controller, in some embodiments, is further adapted to forward the following to the server via the network transceiver: (1) a first unique identifier associated with the patient support apparatus; (2) a second unique identifier associated with the anchor; and (3) a third unique identifier associated with the mobile device.

The server, in some embodiments, is adapted to determine a room number of a room within the healthcare facility in which the patient support apparatus is located based on the second unique identifier.

The server, in some embodiments, may also be configured to instruct the display to display the room number along with the first data and the second data.

The first data, in some embodiments, includes at least one of the following items: a status of a brake onboard the patient support apparatus; a status of an exit detection system onboard the patient support apparatus; a status of a siderail onboard the patient support apparatus; height information of an adjustable height litter frame of the patient support apparatus; an occupancy status of the patient with respect to the patient support apparatus; or a status of a monitoring system onboard the patient support apparatus adapted to monitor a plurality of conditions of the patient support apparatus.

The second data, in some embodiments, includes at least one of the following items: a battery status of the mobile device; a usage metric of the mobile device; a type of device the mobile device is; whether the mobile device is inside or outside of the volume of space; or a time at which the mobile device entered or exited the volume of space.

The controller, in some embodiments, is further adapted to repetitively update the first relative position of the mobile device with respect to the patient support apparatus and to repetitively determine if the device is inside or outside of the volume of space based on the repetitively updated first relative position.

The controller may further be adapted to determine an orientation of the patient support apparatus relative to the wall based on communications between the anchor and the first and second pseudo-anchors.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
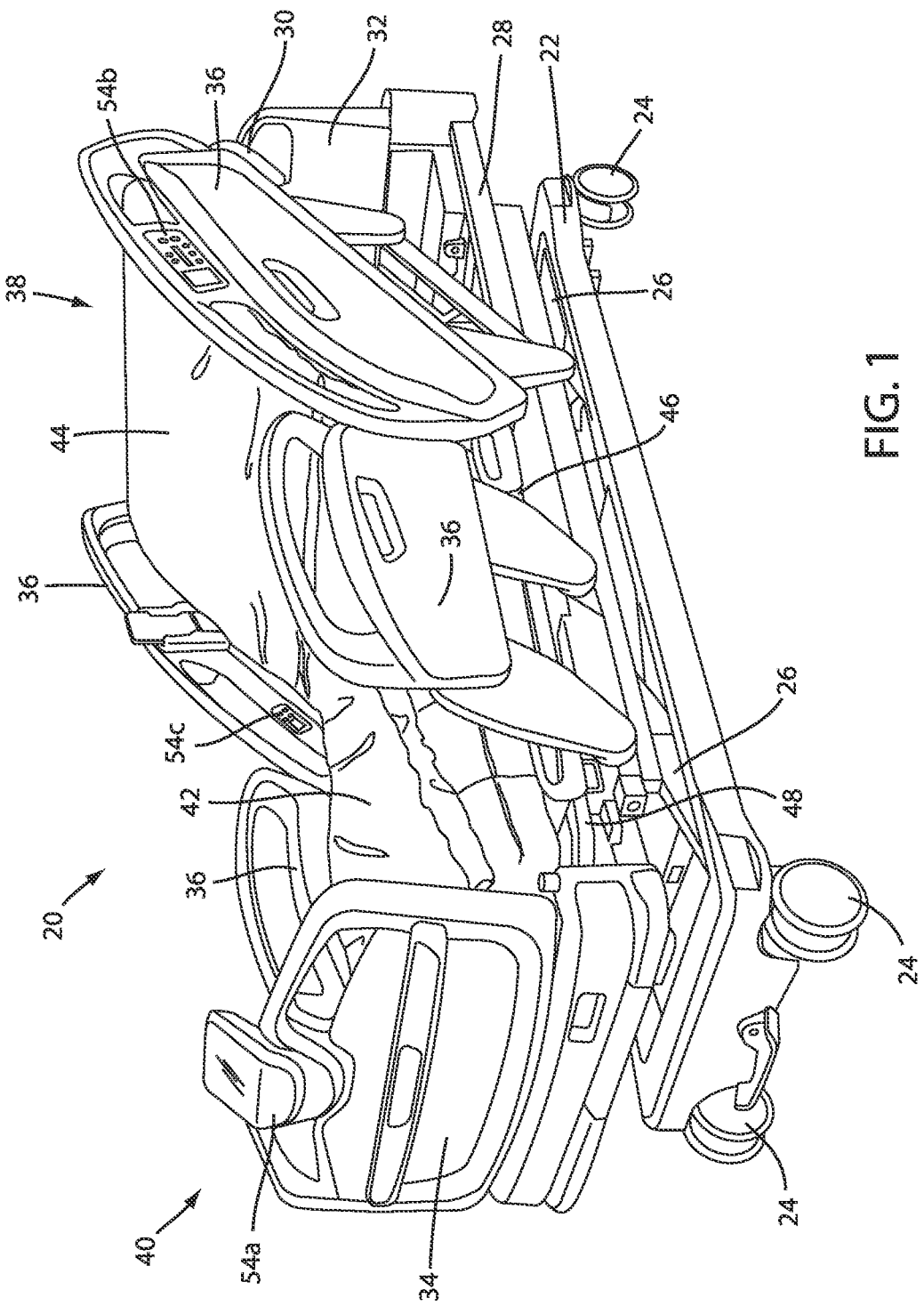
FIG. 1 is a perspective view of a patient support apparatus according to an embodiment of the present disclosure.

An illustrative patient support apparatus 20 according to an embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. In some embodiments, the mattress 42 includes one or more inflatable bladders that are controllable via a blower, or other source of pressurized air. In at least one embodiment, the inflation of the bladders of the mattress 42 is controllable via electronics built into patient support apparatus 20. In one such embodiments, mattress 42 may take on any of the functions and/or structures of any of the mattresses disclosed in commonly assigned U.S. Pat. No. 9,468, 307 issued Oct. 18, 2016, to inventors Patrick Lafleche et al., the complete disclosure of which is incorporated herein by reference. Still other types of mattresses may be used.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of mechanical constructions that are different from what is shown in the attached drawings, such as, but not limited to, the construction described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may include the same, or nearly the same, structures as the Model 3002 S3 bed manufactured and sold by Stryker Corporation of Kalamazoo, Michigan. This construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. In still another embodiment, the mechanical construction of patient support apparatus 20 may include the same, or nearly the same, structure as the Model 3009 Procuity MedSurg bed manufactured and sold by Stryker Corporation of Kalamazoo, Michigan. This construction is described in greater detail in the Stryker Maintenance Manual for the 3009 Procuity MedSurg bed (publication 3009-009-002, Rev. A.0), published in 2020 by Stryker Corporation of Kalamazoo, Michigan.

It will be understood by those skilled in the art that patient support apparatus 20 can be designed with still other types of mechanical constructions, such as, but not limited to, those described in commonly assigned, U.S. Pat. No. 7,690, 059 issued Apr. 6, 2010, to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The overall mechanical construction of patient support apparatus 20 may also take on still other forms different from what is disclosed in the aforementioned references provided the patient support apparatus includes one or more of the functions, features, and/or other structures discussed in greater detail below.

Figure 2:
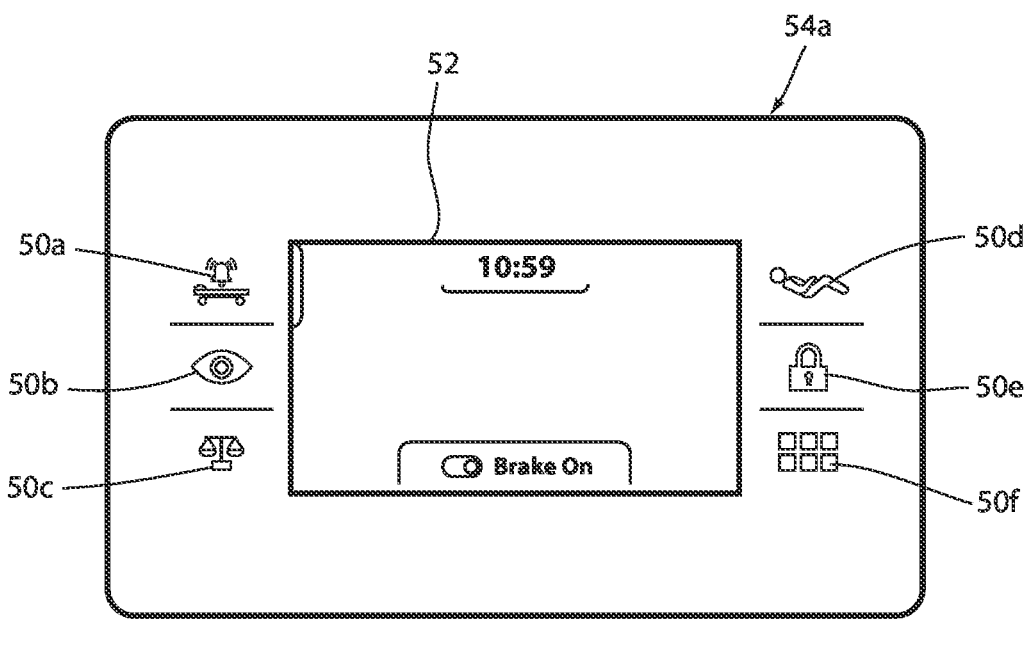
FIG. 2 is a plan view of an illustrative caregiver control panel of the patient support apparatus of FIG. 1.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel 54a, a pair of outer siderail control panels 54b (only one of which is visible), and a pair of inner siderail control panels 54c (only one of which is visible). Footboard control panel 54a and outer siderail control panels 54b are intended to be used by caregivers, or other authorized personnel, while inner siderail control panels 54c are intended to be used by the patient associated with patient support apparatus 20. Each of the control panels 54 includes a plurality of controls 50 (see, e.g. FIGS. 2-3), although each control panel 54 does not necessarily include the same controls and/or functionality.

Among other functions, controls 50 of control panel 54a allow a user to control one or more of the following: change a height of support deck 30, raise or lower head section 44, activate and deactivate a brake for wheels 24, arm and disarm an exit detection system 56 (FIG. 5), change various settings on patient support apparatus 20, view the current location of the patient support apparatus 20 as determined by the location detection system discussed herein, view what devices patient support apparatus 20 has associated itself with, and perform other actions. One or both of the inner siderail control panels 54c also include at least one control that enables a patient to call a remotely located nurse (or other caregiver). In addition to the nurse call control, one or both of the inner siderail control panels 54c also include one or more controls for controlling one or more features of one or more room devices positioned within the same room as the patient support apparatus 20. As will be described in more detail below, such room devices include, but are not necessarily limited to, a television, a reading light, and a room light. With respect to the television, the features that may be controllable by one or more controls 50 on control panel 54c include, but are not limited to, the volume, the channel, the closed-captioning, and/or the power state of the television. With respect to the room and/or night lights, the features that may be controlled by one or more controls 50 on control panel 54c include the on/off state and/or the brightness level of these lights.

Figure 5:
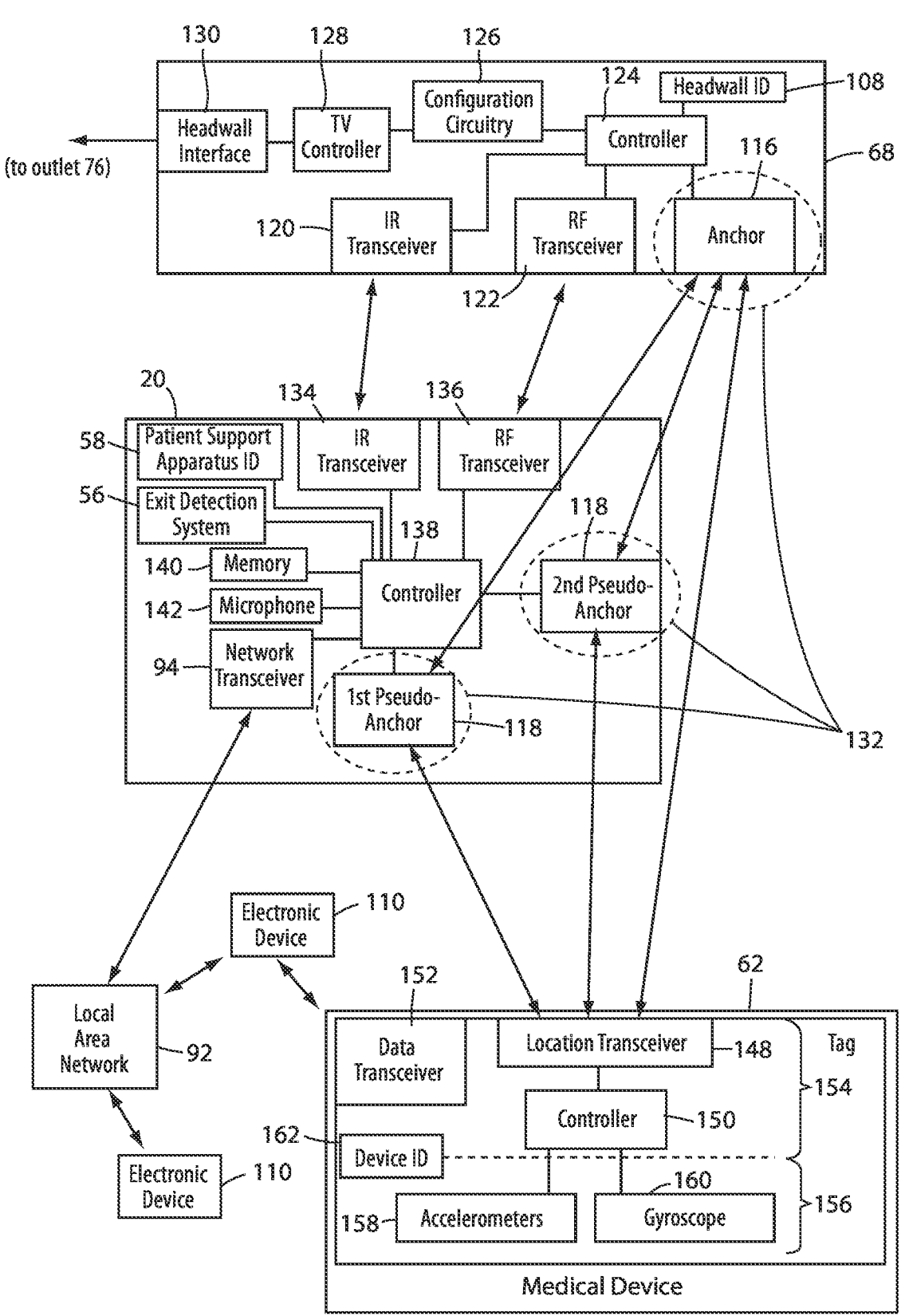
FIG. 5 is a block diagram of several components of the system of FIG. 4.

Control panel 54a includes a display 52 (FIG. 2) configured to display a plurality of different screens thereon. Surrounding display 52 are a plurality of navigation controls 50a-f that, when activated, cause the display 52 to display different screens on display 52. More specifically, when a user presses navigation control 50a, control panel 54a displays an exit detection control screen on display 52 that includes one or more icons that, when touched, control an onboard exit detection system 56 (FIG. 5). The exit detection system 56 is as adapted to issue an alert when a patient exits from patient support apparatus 20. Exit detection system 56 may include any of the same features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. Other types of exit detection systems may be included within patient support apparatus 20.

When a user presses navigation control 50b (FIG. 2), control panel 54 displays a monitoring control screen that includes a plurality of control icons that, when touched, control an onboard monitoring system built into patient support apparatus 20. The onboard monitoring system alerts the caregiver through a unified indicator, such as a light or a plurality of lights controlled in a unified manner, when any one or more of a plurality of settings on patient support apparatus 20 are in an undesired state, and uses that same unified indicator to indicate when all of the plurality of settings are in their respective desired states. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference. Other types of monitoring systems may be included within patient support apparatus 20.

When a user presses navigation control 50c, control panel 54a displays a scale control screen that includes a plurality of control icons that, when touched, control the scale system of patient support apparatus 20. Such a scale system may include any of the same features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference. The scale system may utilize the same force sensors and/or other components that are utilized by the exit detection system 56, or it may utilize one or more different sensors and/or other components. Other scale systems besides those mentioned above in the '254 and '954 applications may alternatively be included within patient support apparatus 20.

When a user presses navigation control 50d, control panel 54 displays a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 in response to pressing control 50d may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference. Other types of motion control screens may be included on patient support apparatus 20.

When a user presses navigation control 50e, control panel 54a displays a motion lock control screen that includes a plurality of control icons that, when touched, control one or more motion lockout functions of patient support apparatus 20. Such a motion lockout functions typically include the ability for a caregiver to use control panel 54a to lock out one or more of the motion controls 50 of the patient control panels 54c such that the patient is not able to use those controls 50 on control panels 54c to control the movement of one or more components of patient support apparatus 20. The motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMI-ZATION, the complete disclosure of which is incorporated herein by reference. Other types of motion lockouts may be included within patient support apparatus 20.

When a user presses on navigation control 50f, control panel 54a displays a menu screen that includes a plurality of menu icons that, when touched, bring up one or more additional screens for controlling and/or viewing one or more other aspects of patient support apparatus 20. Such other aspects include, but are not limited to, displaying information about one or more devices that are currently associated with patient support apparatus 20, diagnostic and/or service information for patient support apparatus 20, mattress control and/or status information, configuration settings, and other settings and/or information. One example of a suitable menu screen is the menu screen 100 disclosed in commonly assigned U.S. patent application Ser. No. 62/885,953 filed Aug. 13, 2019, by inventors Kurosh Naha-vandi et al. and entitled PATIENT SUPPORT APPARATUS WITH TOUCHSCREEN, the complete disclosure of which is incorporated herein by reference. Other types of menus and/or settings may be included within patient support apparatus 20. In at least one embodiment, utilization of navigation control 50f allows a user to navigate to a screen that enables the user to see which devices, if any, are currently located within a predefined volume of space that encompasses patient support apparatus 20. As will be discussed in greater detail below, patient support apparatus 20 includes an onboard locating system that is adapted to automatically determine the relative position of one or more devices with respect to patient support apparatus 20 and, in some instances, automatically associate and/or disassociate those devices with patient support apparatus 20 (and/or the patient assigned to patient support apparatus 20) depending upon whether the device is inside or outside of a volume of space. Further details of this locating system are provided below. In some embodiments, utilization of navigation control 50f may also allow a user to navigate to a screen that enables the user to configure the communication settings between patient support apparatus 20 and a headwall unit 68 (see, e.g. FIGS. 4-5). Examples of the type of communication settings that may be configured in this manner are disclosed in, and illustrated in FIGS. 9-15 of, commonly assigned U.S. patent application Ser. No. 63/26,937 filed May 19, 2020, by inventors Alexander Bodurka et al. and entitled PATIENT SUPPORT APPARATUSES WITH HEADWALL COMMUNICATION, the complete disclosure of which is incorporated herein by reference.

For all of the navigation controls 50a-f (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50a-f. It will also be understood that, although navigation controls 50a-f have all been illustrated in the accompanying drawings as dedicated controls that are positioned adjacent display 52, any one or more of these controls 50a-f could alternatively be touchscreen controls that are displayed at one or more locations on display 52. Still further, although controls 50a-f have been shown herein as buttons, it will be understood that any of controls 50a-f could also, or alternatively, be switches, dials, or other types of non-button controls. Additionally, patient support apparatus 20 may be modified to include additional, fewer, and/or different navigation controls from the navigation controls 50a-f shown in FIG. 2.

Figure 3:
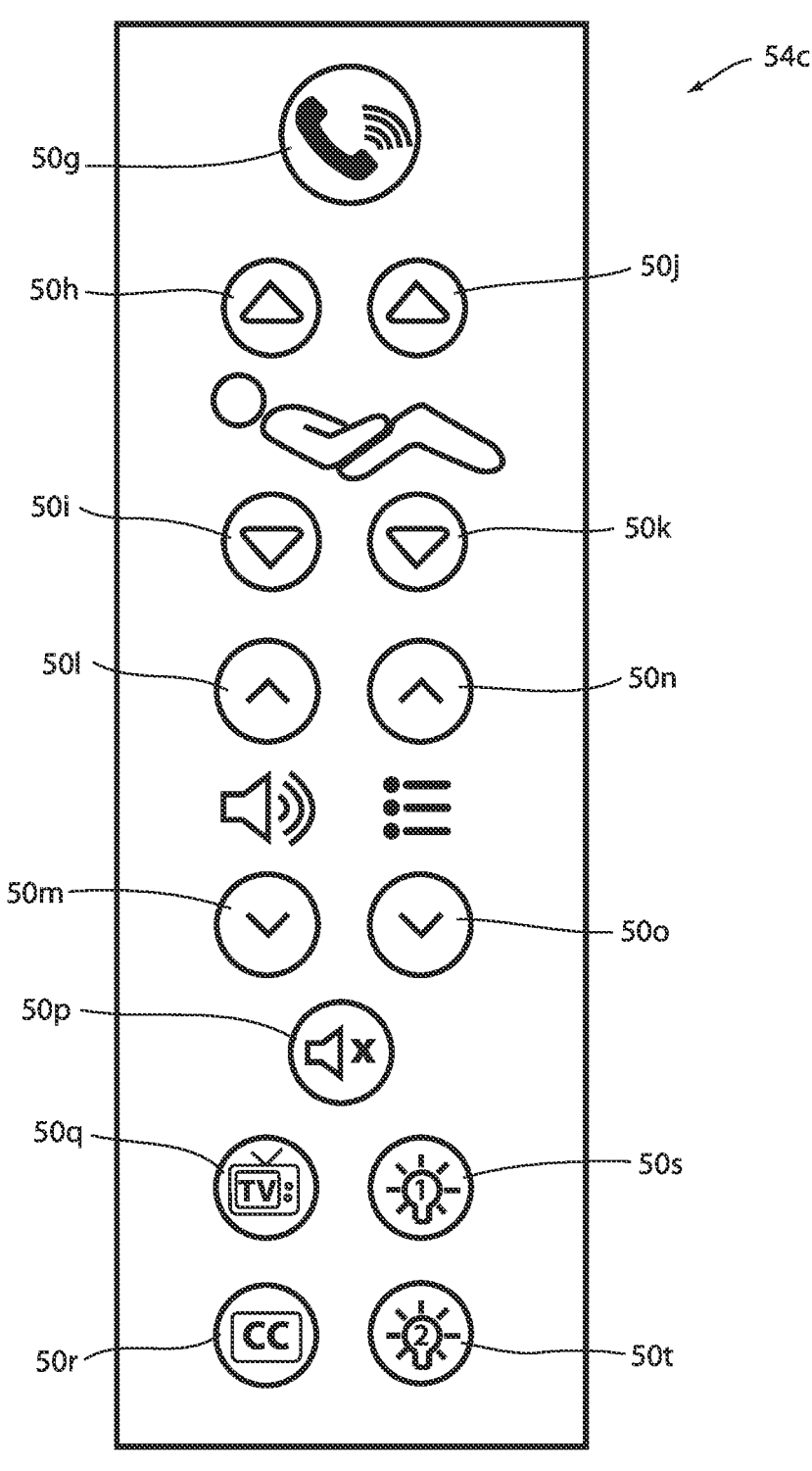
FIG. 3 is a plan view of an illustrative patient control panel of the patient support apparatus of FIG. 1.

FIG. 3 illustrates one example of a patient control panel 54c that may be incorporated into patient support apparatus 20 and positioned at a location on patient support apparatus 20 that is convenient for a patient to access while supported on support deck 30, such as on an interior side of one of the siderails 36. Control panel 54c includes a plurality of controls 50g-t that are intended to be operated by a patient. A nurse call control 50g, when pressed by the patient, sends a signal to a nurse call system requesting that a remotely positioned nurse talk to the patient. A Fowler-up control 50h, when pressed by the patient, causes a motorized actuator onboard patient support apparatus 20 to raise Fowler section 44 upwardly. A Fowler-down control 50i, when pressed by the patient, causes the motorized actuator to lower Fowler section 44 downwardly. A gatch-up control 50j, when pressed by the patient, causes another motorized actuator to raise a knee section of support deck 30, while a gatch-down control 50k causes the motorized actuator to lower the knee section of support deck 30. The knee section may refer to the joint that couples thigh section 46 to foot section 48.

A volume-up control 50l, when pressed by the patient, causes patient support apparatus 20 to send a signal to an in-room television instructing it to increase its volume, while a volume down control 50m, when pressed, causes patient support apparatus 20 to send a signal to the television instructing it to decrease its volume. A channel-up control 50n, when pressed by the patient, causes patient support apparatus 20 to send a signal to the television instructing it to increase the channel number, while a channel-down control 50o, when pressed, causes patient support apparatus 20 to send a signal to the television instructing it to decrease the channel number.

A mute control 50p, when pressed, causes patient support apparatus 20 to send a signal to the television instructing it to either mute itself or unmute itself, depending upon whether the television is currently muted or unmuted. In other words, mute control 50p is a toggle control that alternatingly sends mute and unmute commands to the television when it is pressed.

Power control 50q is a toggle control that, when pressed, sends a signal to the television to either turn on or turn off, depending upon the television's current power status. Closed-captioning control 50r is another toggle control that, when pressed, sends a signal to the television to either turn on its closed-captioning feature or to turn off its closed captioning feature, depending upon whether the closed-captioning feature is currently on or off.

Control 50s is a toggle control that, when pressed, sends a signal to a first light to either turn on or turn off, depending upon the current state of that first light. Control 50t is another toggle control that, when pressed, sends a signal to a second light to either turn on or turn off, depending upon the current state of that second light. In some embodiments, the first light is a reading light and the second light is a room light, both of which are positioned off-board the patient support apparatus 20.

It will be understood that not only the number of controls 50 on control panel 54c, but also the functions of the controls 50 on control panel 54c, the layout of the controls 50 on control panel 54c, and/or other aspects of control panel 54c may be modified from what is shown in FIG. 3. In some embodiments, control panel 54c is implemented on a pendant controller that includes a cable that is plugged into a port on patient support apparatus 20. In other embodiments, one or more of the controls 50 of control panel 54c may be omitted, augmented, and/or split amongst other controls panels and/or locations. Still other manners of implementing control panel 54c are also possible.

Figure 4:
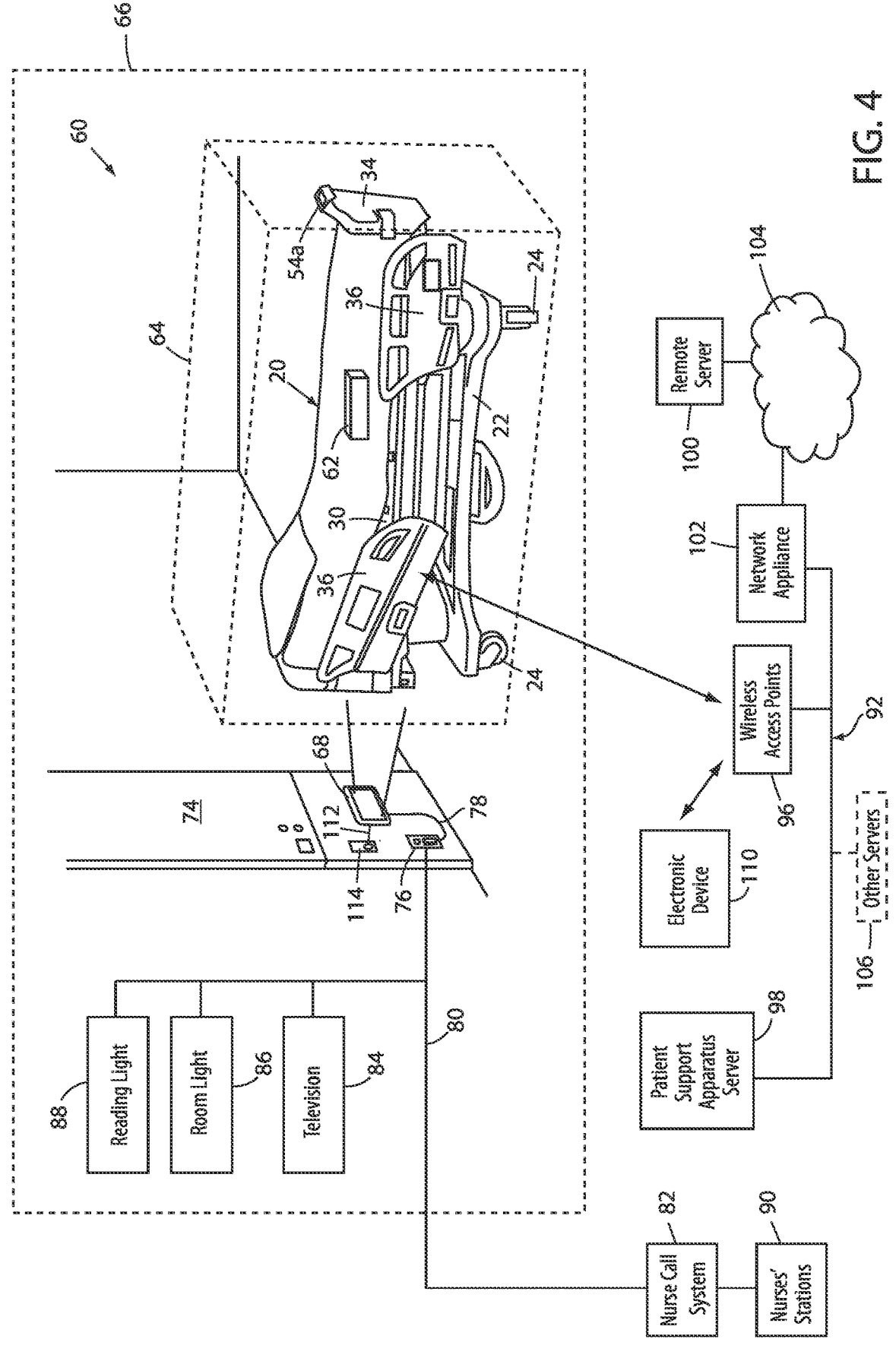
FIG. 4 is a diagram of an embodiment of a system for automatically detecting the position of tagged devices positioned in a room of a healthcare facility.

FIG. 4 illustrates a system 60 for determining the location of one or more devices 62 (that are either tagged with one or more ultra-wideband (UWB) transceivers, or have one or more UWB transceivers built therein), relative to patient support apparatus 20 and/or a volume of space 64 defined within a room 66 of a conventional healthcare facility, such as, but not limited to, a hospital. Such tagged devices 62 include, but are not limited to, exercise devices, heel care boots, IV stands and/or poles, ventilators, patient monitors (e.g. saturated oxygen (SpO$_2$) monitors), vital sign detectors (e.g. heart rate, breathing rate, temperature), patient positioning devices (e.g. wedges, turning devices, pumps), ambient sensors (e.g. air temperature, air flow, light, humidity, pressure, altitude, sound/noise), mattresses, DVT pumps, DVT socks, moisture detection sensors, patient temperature management systems, displays, Holter devices, patient tags, infusion pumps, badges worn by caregivers and/or patients, and/or any other types of devices that are used in the treatment, monitoring, and/or care of the patient.

System 60 includes patient support apparatus 20, one or more headwall units 68, and a combination of one or more anchors 116 and/or pseudo-anchors 118 (see FIG. 5). In some embodiments, one or more servers and/or software applications may be incorporated into system 60. As will be discussed in greater detail below, anchors 116 are positioned at known and fixed locations within the healthcare facility in which patient support apparatus 20 is positioned. Pseudo-anchors 118 are positioned at known and fixed locations on patient support apparatus 20. Thus, although pseudo-anchors 118 do not change their position with respect to the patient support apparatus 20 to which they are attached, pseudo-anchors 118 do change their position within the healthcare facility as the patient support apparatus 20 is moved to different locations. Anchors 116, in contrast, do not change their position within the healthcare facility.

As will be discussed in greater detail below, anchors 116 and pseudo-anchors 118 are adapted to work together to determine if a tagged device 62 is positioned within the volume of space 64. If so, system 60 treats the tagged device 62 in a first manner, and if not, system 60 treats the tagged device 62 in a second and different manner, as will be discussed in greater detail below. In general, if the tagged device is positioned inside the space volume 64, system 60 concludes that the device 62 is associated with the patient assigned to the particular patient support apparatus 20 that is also positioned within the same volume of space 64 (either wholly or partially).

As shown in FIG. 4, room 66 includes a headwall 74 into which a conventional communications outlet 76 is physically integrated. Communications outlet 76 is adapted to receive a nurse call cable 78 that physically connects at its other end either to patient support apparatus 20 (not shown) or to a wireless headwall unit 68 (shown in FIG. 4). In many healthcare facilities, communication outlet 76 includes a 37-pin connector, although other types of connectors are often found in certain healthcare facilities. As will be discussed in greater detail below, headwall unit 68 and nurse call cable 78 allow patient support apparatus 20 to communicate with a nurse call system, and one or more room devices positioned within room 66.

Communication outlet 76 is electrically coupled to one or more cables, wires, or other conductors 80 that electrically couple the communication outlet 76 to a nurse call system 82 and one or more room devices, such as a television 84, a room light 86, and/or a reading light 88. Conductors 80 are typically located behind headwall 74 and not visible. In some healthcare facilities, conductors 80 may first couple to a room interface circuit board that includes one or more conductors 80 for electrically coupling the room interface circuit board to room device 84, 86, 88 and/or nurse call system 82. Still other communicative arrangements for coupling communication outlet 76 to nurse call system 82 and/or one or more room device 84, 86, 88 are possible.

Room device 84, 86, 88 are conventional room devices that are typically present in a conventional hospital room. In most cases, the particular brand and model of the television 84 and/or lights 86, 88 will vary from healthcare facility to healthcare facility, and may vary from room to room within the same healthcare facility. The different models and/or brands of televisions 84, room lights 86, and/or reading lights 88 are often controlled in different manners. For example, the signals that are input into a first brand of television in order to change a channel may require a first voltage level, while the signals that are input into a second brand of television in order to change the channel may require a second voltage level. Still further, apart from differences in voltage levels, the sequence of bits and/or other information that is sent to a television to change the channel, for example, may vary from brand to brand, or from model to model. Still other aspects of the control of the television 84 and/or lights 86, 88 may vary from brand to brand and/or from model to model. Thus, in order for a patient to properly control the television 84 and/or lights 86, 88 using one of the patient control panels 54c, patient support apparatus 20 or headwall unit 68 need to be properly configured to match the particular television 84 and/or lights 86, 88 that are positioned in the same room as the patient support apparatus 20. In the systems described herein, headwall units 68 are configured to match the associated televisions 84 and/or lights 86, 88, as well as the associated nurse call system 82.

Returning to FIG. 4, nurse call cable 78 enables patient support apparatus 20 to communicate with nurse call system 82 and/or room devices 84, 86, 88. A patient supported on patient support apparatus 20 who activates a nurse call control (e.g. 50g; see FIG. 3) on patient support apparatus 20 causes a signal to be wirelessly sent from patient support apparatus 20 to headwall unit 68, which in turn conveys the signal via nurse call cable 78 to the nurse call system 82, which forwards the signal to a one or more remotely located nurses (e.g. nurses at one or more nurse's stations 90). If the patient activates one or more room device controls (e.g. controls 501-t; see FIG. 3), one or more wireless signals are conveyed to headwall unit 68, which in turn sends appropriate signals via nurse call cable 78 to communication outlet 76 and the room device 84, 86, 88 that change one or more features of these devices (e.g. the volume, channel, on/off state, etc.).

As is also shown in FIG. 4, patient support apparatus 20 is further configured to communicate with a local area network 92 of the healthcare facility. In the embodiment shown in FIG. 4, patient support apparatus 20 includes a wireless network transceiver 94 (FIG. 5) that communicates wirelessly with local area network 92. Network transceiver 94 is, in at least some embodiments, a WiFi transceiver (e.g. IEEE 802.11) that wirelessly communicates with one or more conventional wireless access points 96 of local area network 92. In other embodiments, network transceiver 94 may be a wireless transceiver that uses conventional 5G technology to communicate with LAN 92, one or more servers hosted thereon, and/or other devices. In some embodiments, network transceiver 94 may include any of the structures and/or functionality of the communication modules 56 disclosed in commonly assigned U.S. Pat. No. 10,500,401 issued to Michael Hayes and entitled NETWORK COMMUNICATION FOR PATIENT SUPPORT APPARATUSES, the complete disclosure of which is incorporated herein by reference. Still other types of wireless network transceivers may be utilized.

In some embodiments, network transceiver 94 is a wired transceiver that is adapted to allow patient support apparatus 20 to communicate with network 92 via a wired connection, such as an Ethernet cable that plugs into an Ethernet port (e.g. an RJ-45 style port, an 8P8C port, etc.) built into patient support apparatus 20. In still other embodiments, patient support apparatus 20 includes both a wired transceiver 94 for communicating with network 92 via a wired connection and a wireless transceiver 94 for wirelessly communicating with network 92.

Patient support apparatus 20 is configured to communicate with one or more servers on local area network 92 of the healthcare facility. One such server is a patient support apparatus server 98. Patient support apparatus server 98 is adapted, in at least one embodiment, to receive status information from patient support apparatuses 20 positioned within the healthcare facility and distribute this status information to caregivers, other servers, and/or other software applications. As will be discussed in greater detail below, server 106d may also be configured to receive data from one or more devices 62 that are currently associated with patient support apparatus 20 (e.g. that are currently positioned within volume of space 64). In some embodiments, the device(s) 62 first forward their data to patient support apparatus 20 and then patient support apparatus 20 forwards the data to server 106d via its network transceiver 94. In other embodiments, headwall units 68 may include a network transceiver and the device(s) 62 may first forward their data to headwall units 68 (either directly or via patient support apparatus 20), which then forwards the device data to server 106d via its network transceiver. In still other embodiments, the data from the one or more devices 62 may be forwarded, alternatively or additionally, to one or more servers on network 92, such as an Electronic Medical Records (EMR) server, a caregiver assistance server, and/or caregiver assistance software application, as will be discussed in greater detail below.

In some embodiments, patient support apparatus server 98 is configured to communicate at least some of the status data and/or device data received from patient support apparatuses 20 and/or device(s) 62 to a remote server 100 that is positioned geographically remotely from the healthcare facility. Such communication may take place via a conventional network appliance 102, such as, but not limited to, a router and/or a gateway, that is coupled to the Internet 104. The remote server 100, in turn, is also coupled to the Internet

104, and patient support apparatus server 98 is provided with the URL and/or other information necessary to communicate with remote server 100 via the Internet connection between network 92 and server 100.

In some alternative embodiments, patient support apparatus 20 may be configured to communicate directly with one or more cloud-based servers, such as remote server 100, without utilizing patient support apparatus server 98. That is, in some embodiments, patient support apparatuses 20 may be configured to communicate directly with a remote server without relying upon any locally hosted servers (e.g. servers hosted on LAN 92). In one such embodiment, patient support apparatus 20 utilizes Microsoft's Azure could computing service to directly connect to one or more remote servers 100 without utilizing server 106b. In some such embodiments, network appliance 102 is a router configured to support such direct connections. Still other types of direct-to-cloud connections may be utilized with one or more of patient support apparatuses 20. When patient support apparatus 20 is configured to directly communicate with remote server 100, patient support apparatus server 98 may be omitted and any one or more of the functions of patient support apparatus server 98 described herein may be performed by remote server 100.

Patient support apparatus server 98 may also carry out additional functions, such as, but not limited to, determining the location of one or more tagged devices 62 positioned within room 66, and/or processing data received the one or more devices 62. Depending upon whether or not the location of the device 62 is within the volume of space 64 defined with respect to the room 66 or patient support apparatus 20, patient support apparatus server 98 may be configured to determine whether or not to associate the device 62 with a particular patient support apparatus 20, patient, bed bay, room, caregiver, and/or other entity. Patient support apparatus server 98 may further be configured to determine where to route data received from the device 62 depending upon whether it is positioned inside or outside of space volume 64, as well as which depending upon which particular space volume 64 it is positioned inside of (e.g. each of the multiple patient support apparatuses 20 and/or the bays of the healthcare facility may have their own separate space volumes 64 associated with them). In other embodiments, one or more of these functions may be carried out by one or more controllers onboard patient support apparatus 20 or headwall unit 68, and/or a combination of these devices, either alone or in conjunction with server 106b (and/or server 100).

It will be understood that the architecture and content of local area network 92 will vary from healthcare facility to healthcare facility, and that the example shown in FIG. 4 is merely one example of the type of network a healthcare facility may be employ. Typically, one or more additional servers 106 will be hosted on network 92 and one or more of them may be adapted to communicate with patient support apparatus server 98. For example, an electronic health record server 106b (FIG. 13) will typically be present in any healthcare facility, and in some embodiments discussed herein, it will be in communication with patient support apparatus server 98 in order to receive patient data that is to be recorded in a patient's health record (e.g. weight readings taken from the scales built into patient support apparatuses 20; therapies provided to patients using a powered mattress 42 onboard patient support apparatuses 20, data from a device 62 that is determined to be associated with the patient assigned to patient support apparatus 20, etc.). Local area network 92 will also typically allow one or more electronic devices 110 to access the local area network 92 via wireless access points 96. Such electronic devices 110 include, but are not limited to, smart phones, tablet computers, portable laptops, desktop computers, and other types of electronic devices that include a WiFi capability and that are provided with the proper credentials (e.g. SSID, password, etc.) to access network 92 (and, in at least some situations, patient support apparatus server 98).

Headwall units 68 are adapted to wirelessly receive signals from patient support apparatus 20 and deliver the signals to communications outlet 76 in a manner that matches the way the signals would otherwise be delivered to communications outlet 76 if a conventional nurse call cable 78 were connected directly between patient support apparatus 20 and communications outlet 76. In other words, patient support apparatus 20 and headwall unit 68 cooperate to provide signals to communications outlet 76 in a manner that is transparent to communications outlet 76 such that outlet 76 cannot detect whether it is in communication with patient support apparatus 20 via a wired connection or it is in communication with patient support apparatus 20 via a wireless connection between patient support apparatus 20 and headwall unit 68 (the latter of which is in wired communication with outlet 76). In this manner, a healthcare facility can utilize the wireless communication abilities of one or more patient support apparatuses 20 without having to make any changes to their existing communication outlets 76.

In addition to sending signals received from patient support apparatus 20 to communications outlet 76, headwall units 68 are also adapted to forward signals received from communications outlet 76 to patient support apparatus 20. Headwall units 68 are therefore adapted to provide bidirectional communication between patient support apparatus 20 and communications outlet 76. This bidirectional communication includes, but is not limited to, communicating command signals from any of controls 50 and/or from any of electronic devices 110 to corresponding room devices 84, 86, and/or 88 and communicating audio signals between a person supported on patient support apparatus 20 and a caregiver positioned remotely from patient support apparatus 20. The audio signals received by headwall units 68 from a microphone on patient support apparatus 20 are forwarded to communications outlet 76, and the audio signals of a remotely positioned nurse that are received at communications outlet 76 (from nurse call system 82) are forwarded to a speaker onboard patient support apparatus 20.

Nurse call cable 78, in some embodiments, includes a conventional 37 pin connector on each end, one of which is adapted to be inserted into outlet 76 and the other one of which is adapted to be inserted into headwall unit 68. Such 37 pin connections are one of the most common types of connectors found on existing headwalls of medical facilities for making connections to the nurse call system 82 and room devices 84, 86, and 88. Headwall unit 68 and nurse call cable 78 are therefore configured to mate with one of the most common type of communication outlets 76 used in medical facilities. Such 37 pin connectors, however, are not the only type of connectors, and it will be understood that headwall unit 68 can utilize different types of connectors that are adapted to electrically couple to different types of nurse call cables 78 and/or different types of communication outlets 76. One example of such an alternative communications outlet 76 and cable 78 is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication outlets 76 and corresponding connectors may be utilized.

Headwall unit 68 (FIG. 4) also includes an electrical cord 112 having a plug positioned at a far end that is adapted to be inserted into a conventional electrical outlet 114. Electrical cord 112 enables headwall unit 68 to receive power from the mains electrical supply via outlet 114. It will be appreciated that, in some embodiments, headwall unit 68 is battery operated and cord 112 may be omitted. In still other embodiments, headwall unit 68 may be both battery operated and include cord 112 so that in the event of a power failure, battery power supplies power to headwall unit 68, and/or in the event of a battery failure, electrical power is received through outlet 114.

In addition to any of the structures and functions described herein, headwall units 68 may be configured to communicate location data to patient support apparatus 20 that enables patient support apparatus 20 and/or patient support apparatus server 98 to determine the location of patient support apparatus 20 within the healthcare facility. In general, such location determination is carried out by patient support apparatus 20 analyzing wireless signals communicated between itself and headwall unit 68 in order to determine its position relative to headwall unit 68. If patient support apparatus 20, or a predefined reference point on patient support apparatus 20 (e.g. its head end) is positioned within a threshold distance of headwall unit 68, patient support apparatus 20 associates itself with the headwall unit 68. When associated, patient support apparatus 20 communicates data to headwall unit 68, receives data from headwall unit 68, and also deems its location within the healthcare facility to be the same as the location of the associated headwall unit 68. When patient support apparatus 20 is outside of the threshold distance, it does not associate itself with headwall unit 68 (or disassociates itself, if it was previously associated), and therefore does not exchange data with headwall unit 68 or consider its location to be the same as that of headwall unit 68's location.

In some embodiments, patient support apparatus 20 is configured to associate itself with a particular headwall unit 68 if both the patient support apparatus 20 (or a reference point thereon) and headwall unit 68 are concurrently positioned within a common volume of space 64. In some embodiments, the volume of space is defined with respect to each headwall unit 68 and does not move. In other embodiments, the volume of space is defined with respect to patient support apparatus 20 and moves as patient support apparatus 20 moves. In both embodiments, patient support apparatus 20 associates itself with a nearby headwall unit 68 if both the headwall unit 68 and the patient support apparatus 20 (or a reference point thereon) are concurrently within the predefined volume of space.

After associating itself with a particular headwall unit 68, patient support apparatus 20 is configured to be able to have its absolute position within the healthcare facility determined by receiving a unique headwall identifier (ID) 108 (FIG. 5) from the headwall unit 68. The location of each headwall unit 68 in the healthcare facility is surveyed during the installation of headwall units 68, and the unique IDs 108 of each headwall unit 68 are also recorded during the installation of headwall unit 68. This surveying information and corresponding ID information may be stored in patient support apparatus server 98 and/or onboard patient support apparatus 20, thereby enabling patient support apparatus 20 and/or patient support apparatus server 98 to determine the location of a patient support apparatus 20 once it is associated with a particular I headwall unit 68.

In those embodiments where patient support apparatus server 98 is configured to determine the location of patient support apparatus 20, patient support apparatus 20 sends its relative position information and/or the ID 108 of the associated headwall unit 68 (and its own unique patient support apparatus ID 58 (FIG. 5)) to server 98. Server 98 includes a table of all of the locations of the headwall unit 68 (which, as noted, is generated via a surveying operation during the installation of headwall units 68), and it uses that table to correlate the patient support apparatus IDs 58 and the headwall unit IDs 108 it receives to specific locations within the healthcare facility. Thus, if a particular patient support apparatus 20 (with a particular ID 58) sends an associated headwall unit ID 108 that corresponds to room 430, server 98 determines that that particular patient support apparatus 20 is currently located in room 430. Generally speaking, and as will be discussed in greater detail below, the location of a patient support apparatus 20 is deemed to correspond to whichever headwall unit 68 it is currently associated with, and if it is not currently associated with any headwall unit 68, its location may be considered to be indeterminate. The above-described location-determination process is described in greater detail in—and may include any of the features or functions described in—commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

Headwall units 68 may also perform additional functions. In some embodiments, headwall units 68 may perform any of the functions performed by the headwall units 76 disclosed in commonly assigned U.S. patent application Ser. No. 16/215,911 filed Dec. 11, 2018, by inventors Alexander Bodurka et al. and entitled HOSPITAL HEADWALL COMMUNICATION SYSTEM, the complete disclosure of which is incorporated herein by reference. In some embodiments, headwall units 68 may also, or alternatively, perform any of the same functions performed by the headwall interfaces 72 disclosed in commonly assigned U.S. patent application Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosure of which is also incorporated herein by reference. In still other embodiments, headwall units 68 may also, or alternatively, perform any of the same functions performed by the headwall units 68 disclosed in commonly assigned U.S. patent application Ser. No. 16/217,203 filed Dec. 12, 2018, by inventor Alexander Bodurka et al. and entitled SMART HOSPITAL HEADWALL SYSTEM, the complete disclosure of which is incorporated herein by reference.

In some embodiments, headwall units 68 may be constructed to include any or all of the functionality of the wireless headwall units disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference.

In some embodiments, headwall units 68 may also be constructed to include any or all of the functionality of the headwall units disclosed in commonly assigned U.S. patent application Ser. No. 63/26,937 filed May 19, 2020, by inventors Alexander Bodurka et al. and entitled PATIENT SUPPORT APPARATUSES WITH HEADWALL COM- MUNICATION, the complete disclosure of which is also incorporated herein by reference.

Still further, in some embodiments, headwall units may be constructed to include any of the features and/or functions of the headwall units 144a disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference.

In some embodiments, patient support apparatus 20 and/or patient support apparatus server 98 may include any or all of the functionality of the patient support apparatuses and/or patient support apparatus servers described in any of the aforementioned commonly assigned U.S. patents and/or patent applications.

FIG. 5 depicts a block diagram of various components of one embodiment of system 60. These include a patient support apparatus 20 having one or more pseudo-anchors 118, a headwall unit 68 having at least one anchor 116, and a tagged device 62. It will be understood that the components depicted in FIG. 5 are not necessarily a complete set of components, and that system 60 may additionally include one or more additional anchors 116 and/or pseudo-anchors 118, one or more patient support apparatuses 20, and/or one or more additional headwall units 68. Further, it will be understood that the internal circuitry of each of these components may include more than what is shown in FIG. 5. For example, while headwall unit 68 is depicted in FIG. 5 to include only a single anchor 116, it will be understood that it may include more than one of these. Similarly, although patient support apparatus 20 is depicted as including two pseudo-anchors 118, it may include more or less than these two. Still other variations of system 60 are possible, including, but not limited to, variations having fewer components than those shown in FIG. 5. Still further, system 60 may include, in at least some embodiments, one or more servers on local area network 92 that may or may not be in communication with one or more other servers on network 92 and/or with one or more remote electronic devices 110.

Figure 13:
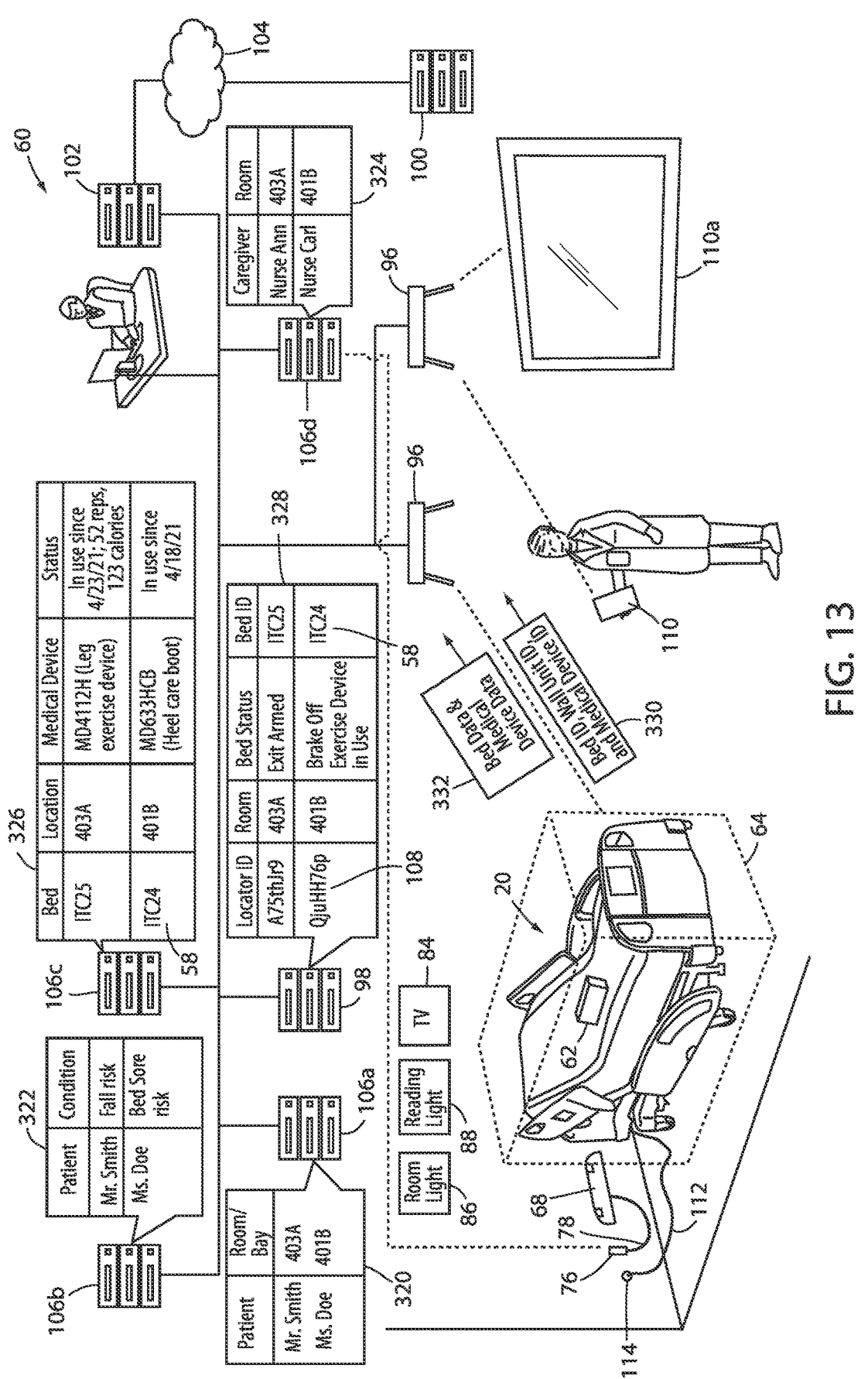
FIG. 13 is a diagram of the system of FIG. 4 showing more details of a plurality of servers that may be resident in a healthcare facility.

As was noted, system 60 is adapted to determine if one or more devices 62 are positioned within one or more predefined volumes of space 64 (FIGS. 4 & 13). The predefined volume of space (or spaces) may be defined in a fixed manner relative to the dimensions of the room 66 (and thus stationary), or it may be defined relative to patient support apparatus 20 (and thus moveable as patient support apparatus 20 moves). When defined in fixed manner, volume 64 will typically include the space defined by a particular bay within the room 66. That is, it will encompass the volume typically occupied by the patient support apparatus 20 when the patient support apparatus 20 is in its customary position within a particular bay within the room 66. It will also typically encompass a relatively small amount of space surrounding the customary position of the patient support apparatus 20 (such as, but not limited to, about one to two feet beyond the perimeter of the patient support apparatus 20) in which devices 62 might be placed that are used with the patient on patient support apparatus 20 (e.g. an IV stand, an exercise device, a patient monitor, etc.). In some embodiments, different volumes of space 64 may be defined for different devices, and patient support apparatus 20 may automatically select which volume of space 64 to use for a particular device based upon an ID of the device that the device forwards to patient support apparatus 20.

Although FIG. 4 depicts volume 64 as a generally rectangular volume, it will be understood that this is merely one example of the shape that volume 64 may take on. Other non-rectangular shapes and/or shapes having portions that are rectangular and portions that are non-rectangular, as well as still other shape combinations, may be used. Volume 64 generally corresponds to the volume of space in which a device 62 must be positioned in order for system 60 to associate it with that particular patient support apparatus 20 (and/or with the patient assigned to that patient support apparatus 20 and/or with the bay or room to which that patient is assigned).

In some embodiments, regardless of whether volume of space 64 is fixed or mobile, the size and/or shape of space volume 64 may be dynamic. That is, the size and/or shape of space 64 may vary in some embodiments. This size and/or shape variance may be based on one or more of the following factors: (a) the particular type, brand, model, or other characteristic of patient support apparatus 20; (b) the particular room, bay, or other environment in which patient support apparatus 20 is currently located; (c) the particular tagged device 62 whose location is being determined; and/or (d) the relative proximity of another patient support apparatus 20. Thus, for example, system 60 is configured in some embodiments to assign larger space volumes 64 to certain models of patient support apparatus 20 that are larger than other models of patient support apparatuses 20. As another example, system 60, in some embodiments, alters the shape and/or enlarges the size of volume 64 in private hospital rooms when compared to the volume 64 that it utilizes in semi-private hospital rooms in which another patient support apparatus 20 is located. Still further, for example, system 60 may utilize larger space volumes 64 for devices 62 that are customarily positioned alongside patient support apparatus 20 rather than on patient support apparatus 20 (e.g. mobile IV stands that are supported on the floor versus heel care boots that are worn by the patient). As yet another example, system 60, in some embodiments, may reduce the size of, or otherwise change the shape of, volume 64 when a patient support apparatus 20 is positioned in relatively close proximity to another patient support apparatus 20 in order to avoid mistakenly assigning a tagged device 62 to the nearby, but incorrect, patient support apparatus 20. Still other examples of changing the size and/or shape of space volume 64 may be implemented.

As was noted, volume of space 64 is predefined. The term "predefined" herein means that the criteria used for setting the size, shape, and/or location of space volume 64 are programmed into the components of system 60 during manufacture, during a user-customization process, or during a software update. Thus, although this programming may include the ability for the size, shape, and/or location of space volume 64 to change in any of the manners noted above, such changes are carried out in a known manner according to the programming of the components of system 60.

Headwall unit 68 (FIG. 5), in some embodiments, includes an infrared transceiver 120, a Bluetooth transceiver 122, a headwall unit controller 124, configuration circuitry 126, smart television control circuitry 128, and a headwall interface 130. Headwall unit 68 also includes at least one anchor 116 that, as will be described more below, is used in conjunction with pseudo-anchors 118 (and/or one or more other anchors 116) to form a location engine 132 that is configured to determine the location of device 62. Infrared transceiver 120 is adapted to communicate with an infrared transceiver 134 of patient support apparatus 20 using infrared waves. Bluetooth transceiver 122 is adapted to communicate with Bluetooth transceiver 136 of patient support apparatus 20 using RF waves in accordance with the conventional Bluetooth standard (e.g. IEEE 802.14.1 and/or the standard maintained by the Bluetooth Special Interest Group (SIG) of Kirkland, Washington, USA). In some embodiments, transceivers 122 and 136 utilize Bluetooth Low Energy communications.

Anchor 116, which may be an ultra-wideband transceiver, is adapted to communicate with one or more pseudo-anchors 118 (which may also be ultra-wideband transceivers) positioned onboard patient support apparatus 20. Anchor 116 is adapted to determine a distance between itself and patient support apparatus 20. Alternatively, or additionally, anchor 116 may be adapted to allow one or more of the pseudo-anchors 118 onboard patient support apparatus 20 to determine their distance(s) from anchor 116. In some embodiments, anchor 116 and pseudo-anchors 118 use time of flight (TOF) computations to determine these distances. In other embodiments, anchor 116 and pseudo-anchors 118 may utilize other techniques for determining their distances from each other, either in addition to, or in lieu of, TOF computations. In some embodiments, anchor 116 and pseudo-anchors 118 may also determine angles between themselves using angular information derived from antenna arrays positions onboard anchor 116 and pseudo-anchors 118, or by using other techniques. The position and orientation of each pseudo-anchors 118 onboard patient support apparatus 20 is known and stored in an onboard memory 140 and used to determine the position and orientation of patient support apparatus 20 with respect to the headwall unit 68 with which it is communicating.

Headwall unit controller 124 is adapted to control the operation of transceivers 120, 122, configuration circuitry 126, TV controller 128, headwall interface 130, and anchor 116. Anchor 116, either alone or conjunction with controller 124, is adapted to determine the distance (as well as angular information, in some embodiments) between itself and one or more pseudo-anchors 118 positioned onboard one or more patient support apparatuses 20. System 60 uses this distance and angular information to repetitively compute the location of tagged device 62 and to repetitively determine whether or not it is inside or outside of space volume 64. In some embodiments, anchor 116, as well as the pseudo-anchors 118, use ultra-wideband transceivers for communicating with each other and determining their relative positions with respect to each other. In other embodiments, anchors 116 and pseudo-anchors 118 use Bluetooth Low Energy transceivers for communicating with each other and determining their relative positions with respect to each other. In still other embodiments, anchor 116 and pseudo-anchors 118 may use both RF and ultra-wideband transceivers. In those embodiments where anchor 116 includes a Bluetooth communication transceiver, this transceiver may be combined with RF transceiver 122 such that it is used both for communicating with patient support apparatus 20 and for determining relative positions of the pseudo-anchors 118. The anchors 116 and pseudo-anchors 118 may include an array of antennas that are used to assist in the determination of location. Different manners in which the structures 116, 118 may determine the location of tagged device 62 are discussed in greater detail in commonly assigned U.S. patent application Ser. No. 63/132,514 filed Dec. 31, 2020, by inventors Alexander Bodurka et al. and entitled PATIENT SUPPORT APPARATUS AND MEDICAL DEVICE NETWORKS, as well as commonly assigned U.S. patent application Ser. No. 63/161,175 filed Mar. 15, 2021, by inventors Krishna Bhimavarapu et al. and entitled EXERCISE DEVICE AND PATIENT SUPPORT APPARATUS, the complete disclosures of both of which are incorporated herein by reference.

In some embodiments, anchors 116 and pseudo-anchors 118 are implemented as any of the Trimension™ ultra-wideband modules available from NXP Semiconductors of Austin, Texas. These modules include, but are not limited to, the Trimension™ UWB modules ASMOP1BO0N1, ASMOP1CO0R1, and/or the ASMOP1CO0A1, that utilize any of the following chips: the NXP SR150, SR100T, SR040, NCJ29D5, and/or the OL23DO chips. Modules manufactured and/or marketed by other companies may also be used, including, but not limited to, the Decawave DWM1000, DWM10001C, DWM3000 modules (available from Decawave of Dublin, Ireland); the Nordic TSG5162 SiP module (available from Tsingoal Technology of Beijing, China); and/or the UWB hub, wand, and/or sensors available from Zebra technologies of Lincolnshire, Illinois. Still other types of UWB and/or Bluetooth modules may be used to implement anchors 116 and pseudo-anchors 118.

Patient support apparatus 20 includes a controller 138, a memory 140, the transceivers 134, 136 mentioned above, network transceiver 94, exit detection system 56, a microphone 142, and one or more pseudo-anchors 118. As was noted previously, network transceiver 94 may be a WiFi transceiver, or other type of transceiver, that is adapted to communicate with local area network 92. Each pseudo-anchor 118 onboard patient support apparatus 20 is positioned at a known location on patient support apparatus 20. This known location information is stored in memory 140 and/or elsewhere, and may be defined with respect to any suitable common frame of reference. The known location information may include the spatial relationship between pseudo-anchors 118 and/or any other components of patient support apparatus 20. For example, in some embodiments, the known location information includes the spatial relationship not only between pseudo-anchors 118, but also the spatial relationships between pseudo-anchors 118 and one or more of the following: the head end 38 of patient support apparatus 20, the foot end of patient support apparatus 20, the sides of patient support apparatus 20, the floor, IR position of transceiver 134, and/or other components and/or landmarks of patient support apparatus 20. In some embodiments, this location information is used to determine the orientation of patient support apparatus 20 with respect to headwall unit 68, headwall 74, another patient support apparatus 20, and/or another object or structure within the healthcare facility.

Controller 138 utilizes pseudo-anchors 118 to determine the relative position of a device 62 with respect to each pseudo-anchor 118. If patient support apparatus 20 is positioned within range of an anchor 116, controller 138 also receives relative position information from that anchor 116 that defines the relative position of device 62 with respect to that anchor. Further, each pseudo-anchor 118 communicates with that anchor 116 to determine its relative position with respect to anchor 116. Controller 138 combines all of these relative position estimates with the onboard location data that defines where pseudo-anchors 118 are positioned onboard patient support apparatus 20. From this combined data, controller 138 determines whether device 62 is positioned inside or outside of space volume 64. The manners in which these relative positions may be determined may vary from embodiment to embodiment based upon which type of ultra-wideband or Bluetooth technology is used with anchors 116 and pseudo-anchors 118. In general, distances and/or angular information that is generated from the communications between anchors and pseudo-anchors may utilize Angle of Arrival (AoA) information, Time of Flight (TOF) information, Channel State Information, Time Difference of Arrival (TDoA) information, Two-Way Ranging (TWR) ranging information, and/or other information to generate this information. In some embodiments, each anchor 116 and pseudo-anchor 118 includes an array of antennas that are used to generate distance and/or angular information with respect to the anchor and/or pseudo-anchor in which it is in communication. Still further, in some embodiments, anchors 116 and/or pseudo-anchors 118 include one or more of their own microcontrollers, and the location of anchors 116, pseudo-anchors 118, and tags 146 attached to device 62 may be determined by these internal microcontrollers without utilizing controller 138. In other embodiments, controller 138 may work in conjunction with the microcontrollers of anchors 116, pseudo-anchors 118, and/or the tags 146 to determine their relative locations to each other.

Patient support apparatus 20 also includes, in at least some embodiments, a microphone 142 that is used to detect the voice of the patient when the patient wants to speak to a remotely positioned nurse. The patient's voice is converted to audio signals by microphone 142 and controller 138 is adapted to forward these audio signals to the communications outlet 76 positioned in headwall 74. When a cable 78 is coupled between patient support apparatus 20 and outlet 76, controller 138 forwards these audio signals to outlet 76 via the cable. When no such cable 78 extends between patient support apparatus 20 and outlet 76, controller 138 wirelessly forwards these audio signals to headwall unit 68 (using transceiver 134 and/or 136) and controller 124 of headwall unit 68 forwards these audio signals to outlet 76. As was noted, outlet 76 is in electrical communication with a conventional nurse call system 82 that is adapted to route the audio signals to the correct nurse's station 90, and/or other location. In some embodiments, microphone 142 acts as both a microphone and a speaker. In other embodiments, a separate speaker may be included in order to communicate the voice signals received from the remotely positioned nurse. In some embodiments, the audio communication between patient support apparatus 20 and communications outlet 76 is carried out in any of the manners, and/or includes any of the structures, disclosed in commonly assigned U.S. patent application Ser. No. 16/847,753 filed Apr. 14, 2020, by inventors Alexander Bodurka et al. and entitled PATIENT SUPPORT APPARATUSES WITH NURSE CALL AUDIO MANAGEMENT, the complete disclosure of which is incorporated herein by reference.

Although FIGS. 4 and 13 only illustrate a single headwall unit 68, it will be understood that a typical healthcare facility will include multiple headwall units 68 positioned at different locations. Typically, at least one headwall unit 68 will be positioned in each patient room of the healthcare facility. If the patient room is intended to be occupied by more than one patient, then additional headwall units 68 may be included so that each patient support apparatus 20 will have a headwall unit 68 that it communicates with via IR transceivers 134, 120 when it is positioned adjacent to that headwall unit.

After the installation of headwall units 68 in a particular healthcare facility, the location of each headwall unit 68 (and their anchors 116) within that facility is recorded. In some embodiments, one or more anchors 116 may be installed in fixed locations that are separate from headwall unit 68. In such embodiments, the locations of these free-standing anchors 116 are also surveyed and recorded. The locations of headwall units 68 and anchors 116 are recorded in a common frame of reference (or converted to a common frame of reference after recordation). Thus, each headwall unit 68 knows its location within the healthcare facility (e.g. the room number, bay number, height and location on the headwall 74, and position and orientation relative to any nearby headwall unit 68 and/or anchors 116). Similarly, each free-standing anchor 116 knows its location within the healthcare facility (e.g. room number, bay number, height and location on whatever wall or other structure it is attached to), as well as its position and orientation relative to any nearby other anchors 116 and/or headwall units 68. The term "nearby" in this context is used to refer to anchors 116 and/or headwall units 68 that are within communication range of each other.

The location information of a particular anchor 116 and/or headwall unit 68 may be stored in a memory onboard that particular device and/or it may be stored in a memory onboard other anchors 116 or headwall units 68, and/or in memory 140 of patient support apparatus 20. A server, such as patient support apparatus server 98, may alternatively or additionally be configured to store this location information. If this location information is only stored locally (e.g. onboard the particular device whose location the information corresponds to), this location information is communicated between anchors 116 and pseudo-anchors 118 as needed in order for these devices to be able to determine their location relative to each other and the location of tagged device 62.

Tagged device 62 includes a tag 146 that forms what is sometimes referred to herein as a free node. Tag 146 includes generally includes the same electronics as pseudo-anchors 118 and/or anchor 116. That is, it includes a location transceiver 148 and a controller 150. The location transceiver 148 may utilize ultra-wideband and/or Bluetooth communication, as discussed above with respect to anchors 116 and pseudo-anchors 118. Tag 146, in at least some embodiments, may also include a separate data transceiver 152 is adapted to communicate with one or more electronic devices 110. Data transceiver 152 may be a conventional Bluetooth transceiver, a WiFi transceiver, or another type of transceiver. In some embodiments, location transceiver 148 may be used both for location-determination purposes and for communicating with electronic devices 110, in which case data transceiver 152 may be omitted.

Tag 146 includes a location sensing module 154 and a data gathering module 156. Location sensing module 154 includes location transceiver 148 and controller 150 (and data transceiver 152, if included). Data gathering module 156 includes one or more sensors that gather information about the operation of device 62. Thus, location sensing module 154 communicates with anchors 116 and/or pseudo-anchors 118 in order for the location of device 62 to be determined, and data gathering module 156 gathers information about the operation of device 62.

In some embodiments, location sensing module 154 may comprise any of the aforementioned UWB and/or BT modules. For example, in some embodiments, tag 146 may be comprised of any of the following modules: the Trimension™ UWB modules ASMOP1BO0N, ASMOP1CO0R1, and/or the ASMOP1CO0A1. In such cases, controller 150 may comprise any of the NXP chips SR150, SR100T, SR040, NCJ29D5, and/or the OL23DO. As another example, location sensing module 154 may comprise the Decawave DWM3000, DWM1001C, or DWM1000 modules, in which case controller 150 may comprise the DW3000 or DW1000 chips. Still other components may be used for location transceiver 148 and controller 150. As will be discussed in greater detail below with respect to FIGS. 16 and 17, the components of location sensing module 154 may be mounted to, or on, a first printed circuit board that is separate from a second printed circuit board on which, or to which, the components of data gathering module 156 may be mounted.

In the embodiment shown in FIG. 5, data gathering module 156 includes one or more accelerometers 158 and one or more gyroscopes 160. It will be understood that this particular selection of sensors for device 62 is merely an illustrative example of the sensors that may be present in data gathering module 156. That is, the particular sensors of data gathering module 156 may vary between different devices 62 and/or different models of devices 62. Thus, the data gathered by data gathering module 156 may vary widely depending upon the particular device 62.

For example, if device 62 is a vital signs monitor, the sensors included with data gathering module 156 will include one or more vital sign sensors, such as a blood pressure sensor, a heart rate sensor, a breathing rate sensor, etc. If device 62 is an exercise device intended to be used by the patient assigned to patient support apparatus 20, the exercise device may include one or more force sensors, accelerometers, gyroscopes, timers, and/or other sensors that detect information about the use of the exercise device (e.g. number of reps, force exerted, calories burned, time used, etc.). Other types of sensors that may be included within device 62 include, but are not limited to, one or more sensors for gathering device usage information, diagnostic data, pharmaceutical data, movement data, time data, sleep data, and/or still other data regarding the patient and/or the device 62 itself. Still further, in some embodiments, device 62 may include one or more redundant sensors whose outputs are utilized as checks on each other to ensure data integrity. Still other types of sensors and/or combinations of sensors may be used.

In some embodiments, data gathering module 156 may be omitted entirely from tags 146. The omission of data gathering module 156 may be particularly suitable for devices 62 that do not have any electrical components (other than tag 146) and/or that do not generate data. For example, if device 62 is a heel care boot intended to treat and/or prevent pressure sores on a patient's heels, the heel care boot may be comprised primarily of cushioning material for the patient's heel and may not include any sensors at all. In such cases, there may not be any data from device 62 to report to electronic device 110, network 92, patient support apparatus 20, or any other devices, other than, for example, the time at which the heel care boot was implemented, whether the heel care boot is inside or outside of space volume 64, and/or other information that can be generated from location module 154 and/or other off-board sensors or devices (e.g. the time at which the heel care boot may be recorded by another device in response to a notification of tag 146's usage that is transmitted by location transceiver 62). One example of a heel care boot that may be used as a device 62 is disclosed in U.S. Pat. No. 7,798,974 issued to Ponsi et al. and entitled HEEL ULCER PREVENTION AND CUSHIONING BOOT, the complete disclosure of which is incorporated herein. Other types of protectors against bed sores may also or additionally be used.

Controller 150 of device 62, like controller 138 of patient support apparatus 20, may take on a variety of different forms. In the illustrated embodiment, each of these controllers is implemented as a conventional microcontroller. However, these controllers may be modified to use a variety of other types of circuits-either alone or in combination with one or more microcontrollers-such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 138 and 150 when carrying out the functions described herein, as well as the data necessary for carrying out these functions, are stored in a corresponding memory that is accessible to that particular controller (e.g. memory 140 for controller 138, and a memory (not shown) for controller 150).

Device 62 also includes a device ID 162 that identifies the type of device that device 62 is (e.g. heel care boot, vital signs monitor, patient monitor, IV stand, therapy device, etc.). Device ID 162 may also or alternatively include an ID that uniquely identifies device 62 such that it can be distinguished from other devices 62 of the same type. Device ID 162 may be stored within location module 154, or data gathering module 156, or a combination of both modules 154 and 154. As will be discussed in greater detail below, device ID 162 is transmitted from device 62 to one or more of the components of location engine 132 (one or more anchors 116 and pseudo-anchors 118), which then forwards the ID 162 to a server and/or electronic device 110. The recipient of the device ID 162 (e.g. one of the servers on network 92) has access to a data table that correlates the ID to a specific type of device, and the recipient can then share the fact that a particular type of device 62 is being used with a patient on a particular patient support apparatus 20. This sharing may be with one or more of the electronic devices 110, thereby enabling the electronic devices 110 to display the type of device being used with a particular patient. Data from data gathering module 156 may also be displayed on the same electronic device 110, thereby giving the viewer real time information about the devices 62 being used with a particular patient support apparatus.

Location engine 132 determines the position of tag 146 relative to space volume 64. From this information controller 138 of patient support apparatus 20 is able to determine whether tag 146 is positioned inside or outside of space volume 64. In other embodiments, the information from location engine 132 is processed by one or more other controllers to determine whether device 62 (and its tag 146) is positioned inside or outside of space volume 64. In addition to determining location, location engine 132 is adapted to receive data from data gathering module 156 and display all or some of it on display 52 of patient support apparatus 20 and/or forward all or some of it to network 92. Algorithms that may be utilized by location engine 132, in at least some embodiments, for determining whether tag 146 is inside or outside of space volume 64 are described in more detail in commonly assigned U.S. patent application Ser. No. 63/154,677 filed Feb. 27, 2021, by inventors Celso Pereira et al. and entitled SYSTEM FOR DETERMINING PATIENT SUPPORT APPARATUS AND MEDICAL DEVICE LOCATION, and U.S. patent application Ser. No. 63/161,175, filed Mar. 15, 2021, by inventors Krishna Bhimavarapu et al. and entitled EXERCISE DEVICE AND PATIENT SUPPORT APPARATUS, the complete disclosures of both of which are incorporated herein by reference.

Figure 6:
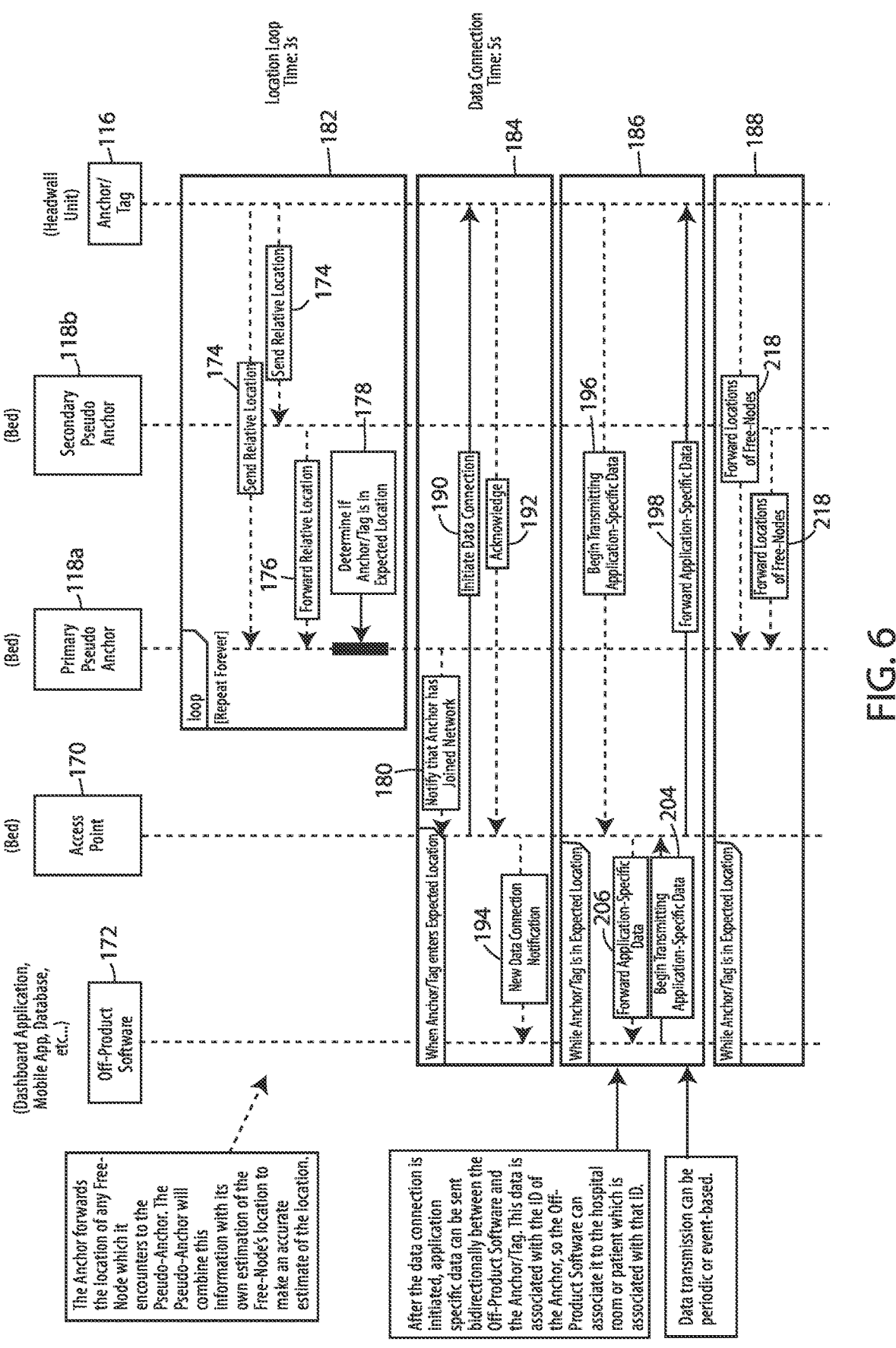
FIG. 6 is a timing diagram illustrating one manner in which several components of the system of FIG. 4 communicate with each other to establish a location engine.
Figure 7:
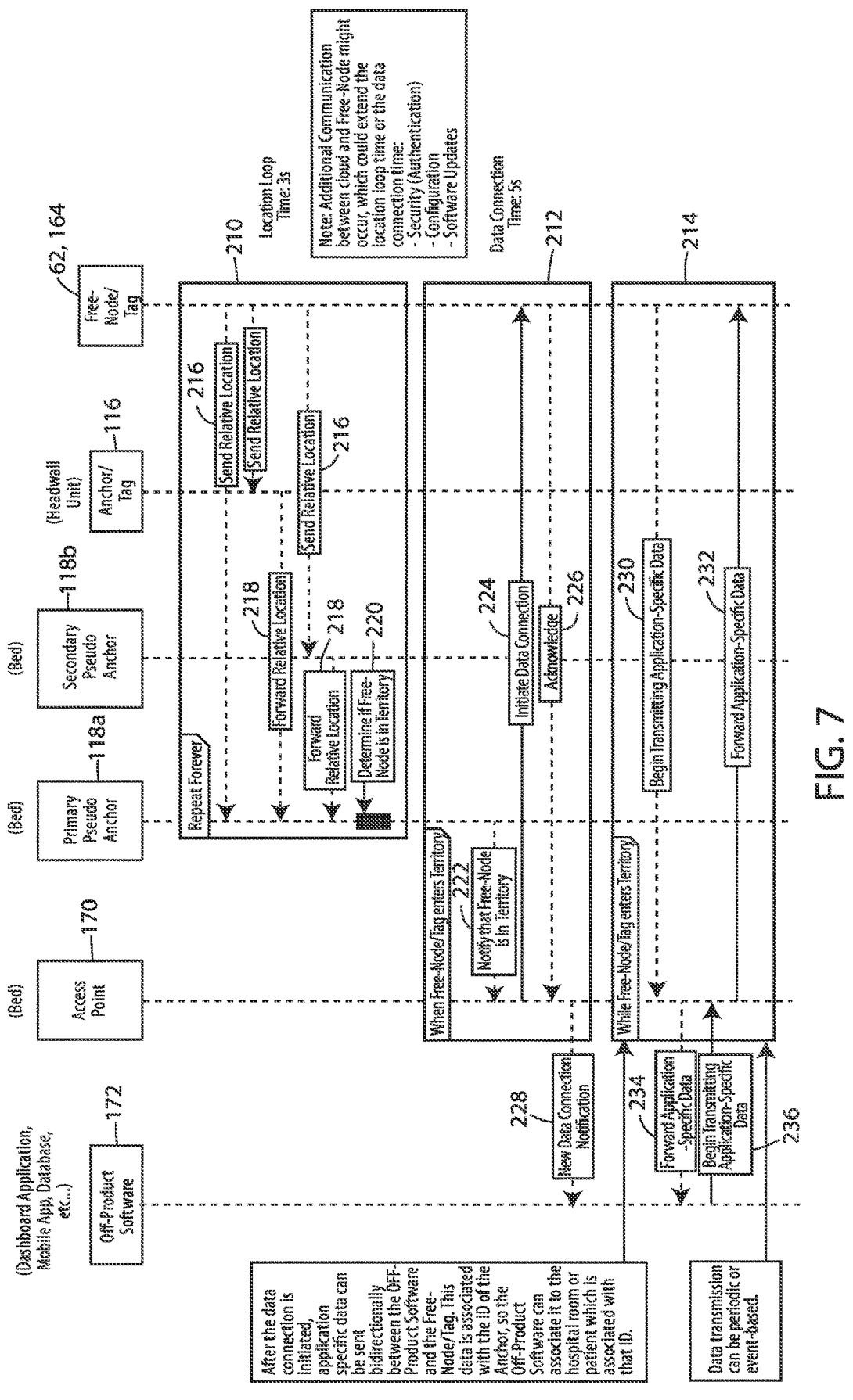
FIG. 7. is a timing diagram illustrating one manner in which communication takes place between the location engine and a mobile device that enters the range of the location engine.
Figure 8:
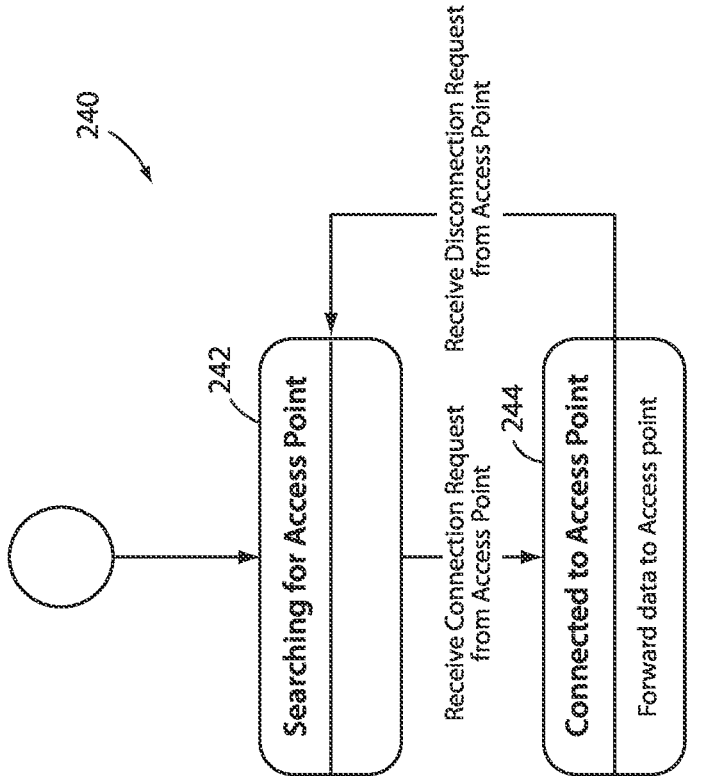
FIG. 8 is a state diagram of an anchor of the location engine.
Figure 9:
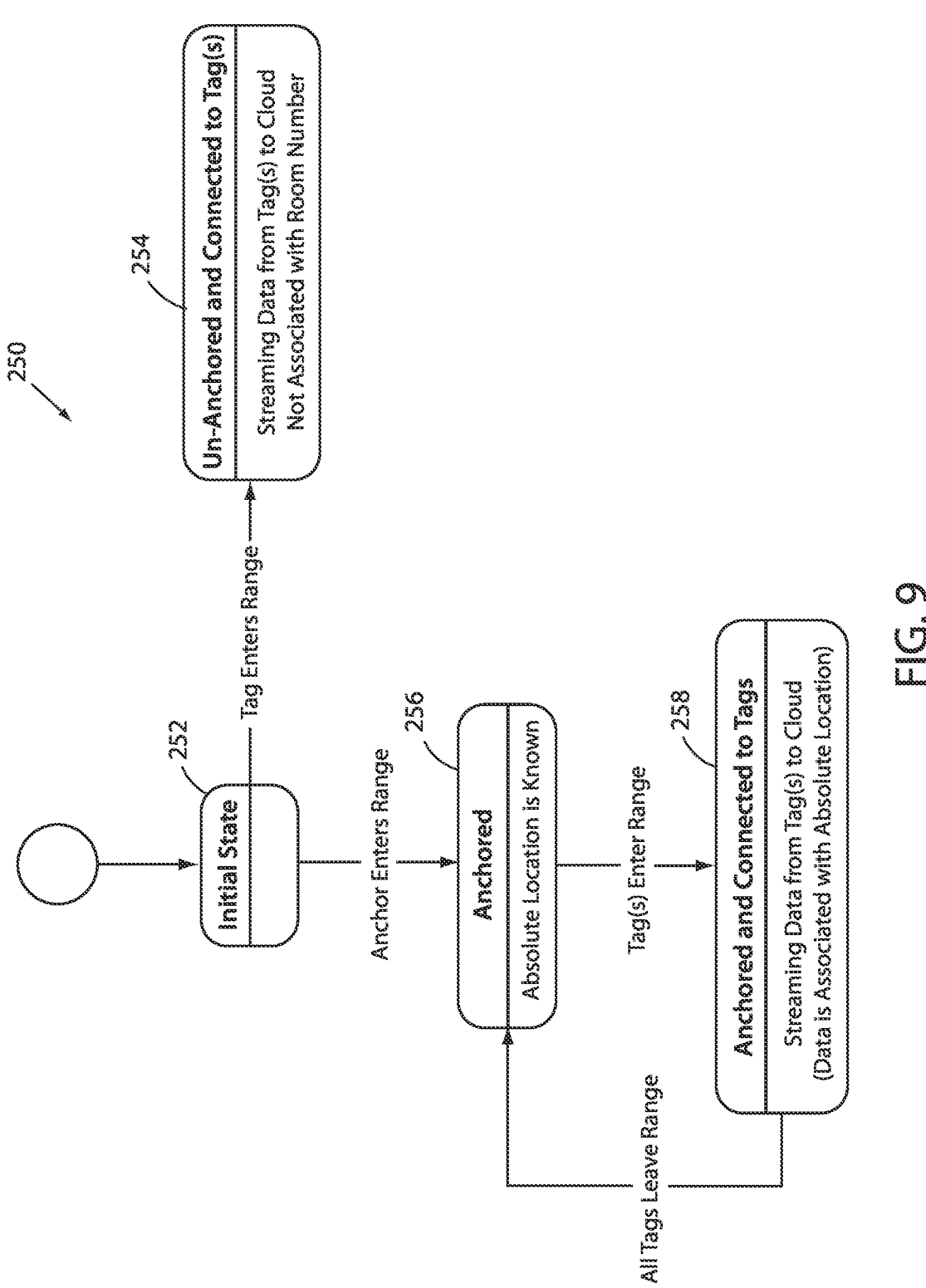
FIG. 9 is a state diagram of the patient support apparatus.
Figure 10:
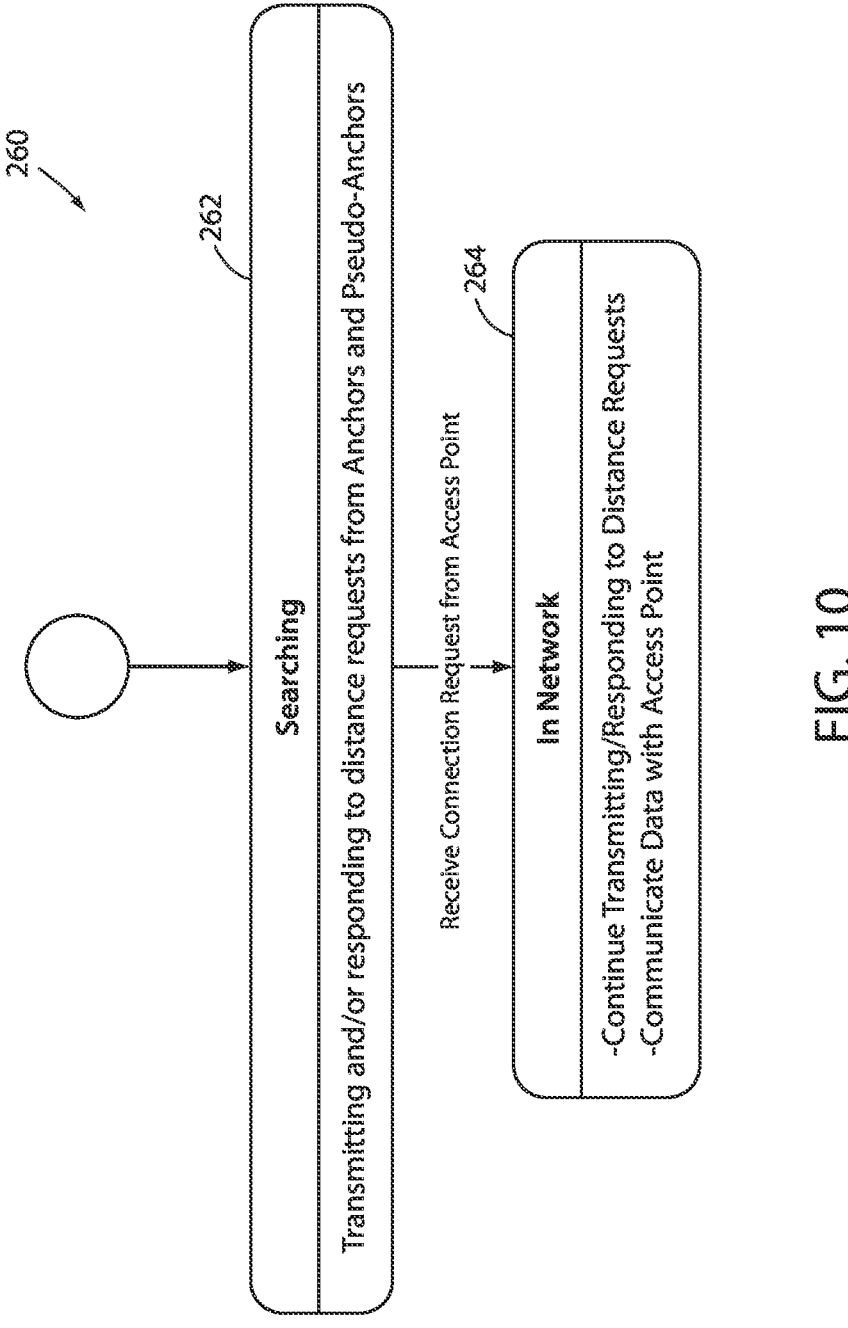
FIG. 10 is a state diagram of the mobile device.
Figure 11:
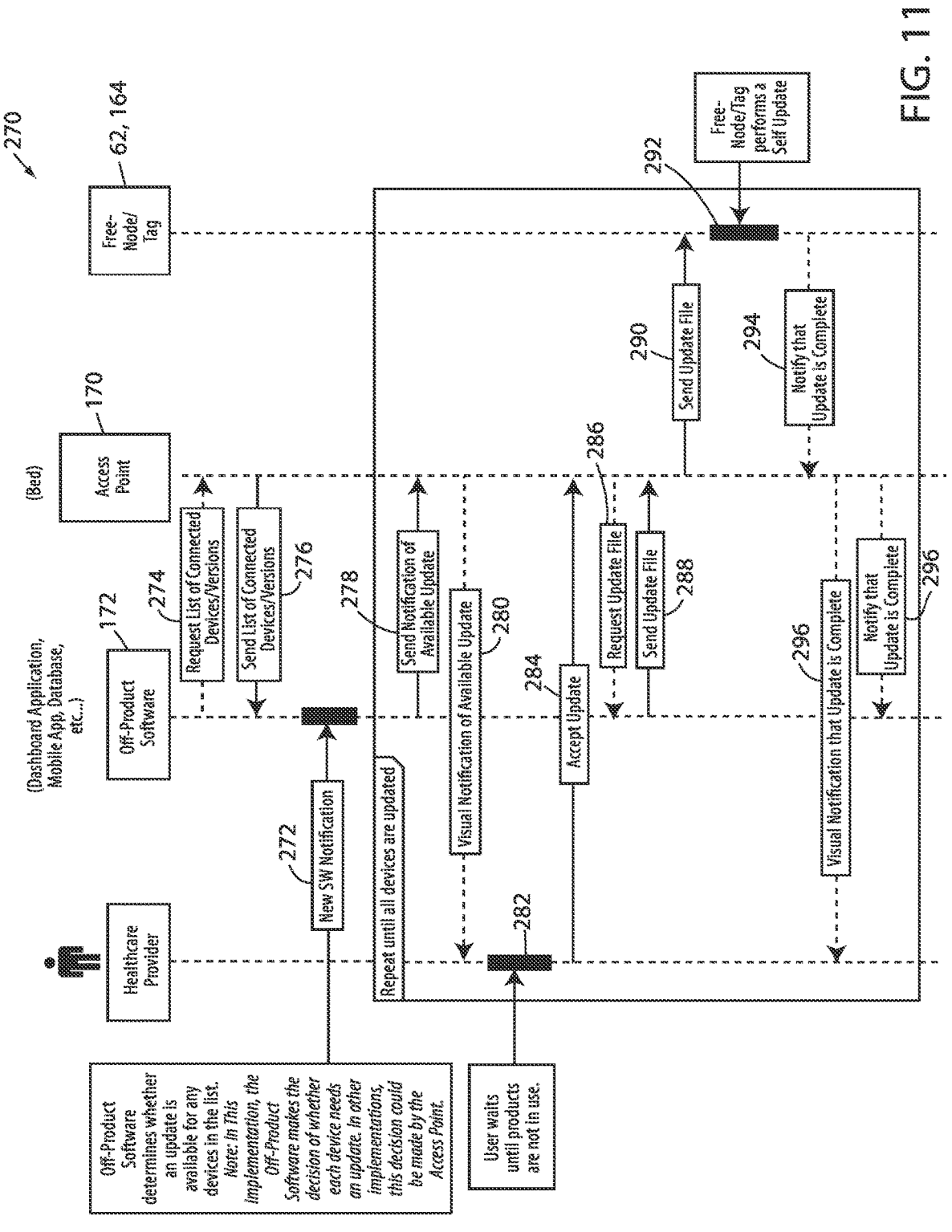
FIG. 11 is a timing diagram of a software updating process that may be used with the components of FIG. 4.
Figure 12:
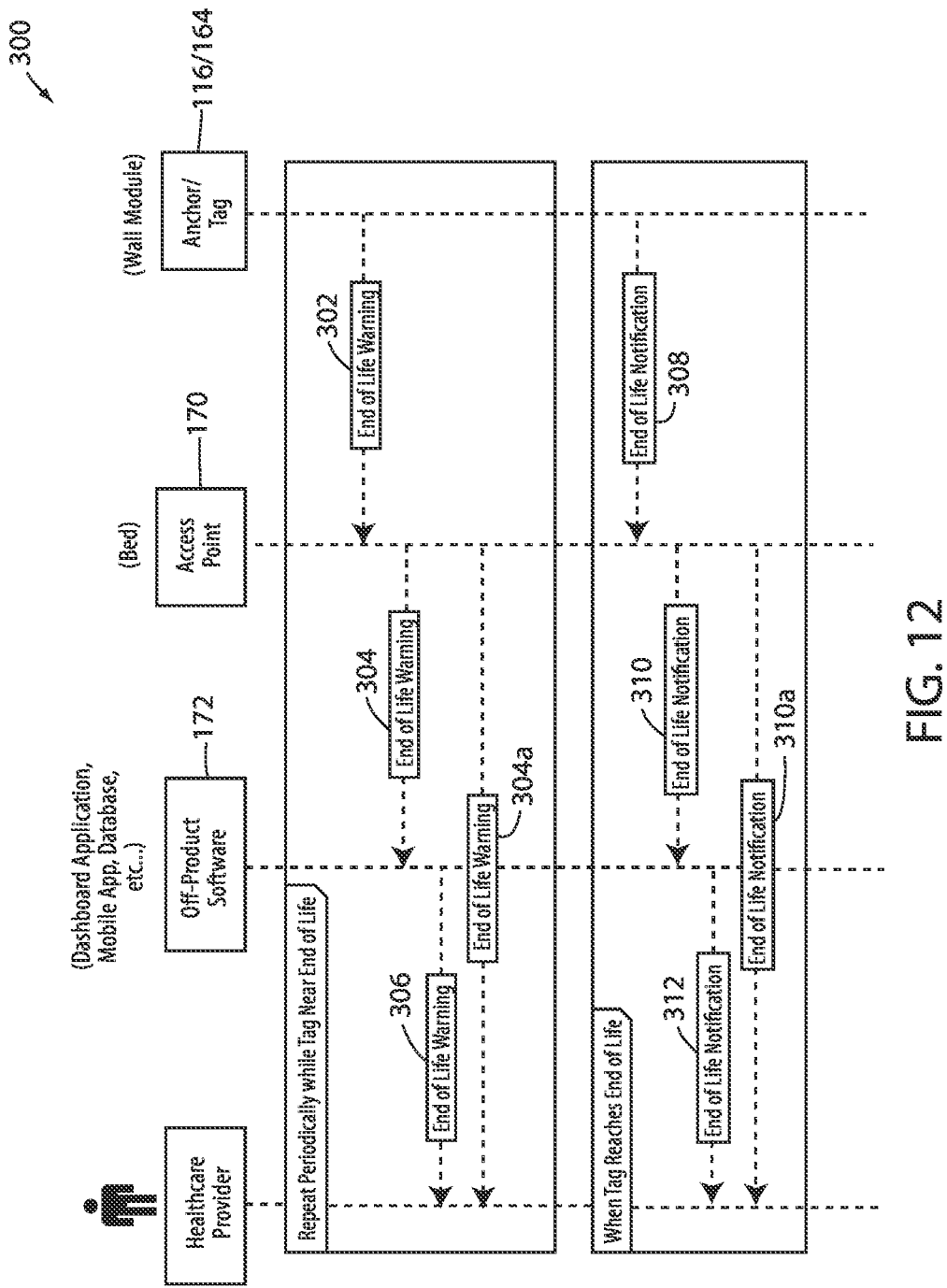
FIG. 12 is an end-of-life timing diagram illustrating one manner in which a mobile device exits from its interactions with the location engine.

FIGS. 6-12 illustrate in greater detail the interactions and operations of the components of location engine 132 and device 62. FIG. 6 illustrates one manner by which location engine 132 is initially formed. FIG. 7 illustrates one manner by which the movement of a tagged device 62 into, or near, space volume 64 is detected. FIG. 8 illustrates the various states of anchor 116. FIG. 9 illustrates the states of the pseudo-anchors 118. FIG. 10 illustrates the states of a tagged device 62. FIG. 11 illustrates a process by which software updates may be forwarded to tag 146 and/or its associated device 62 using the components of system 60. And FIG. 12 illustrates the operation of system 60 when a tag 146 nears its end of life (e.g. its onboard battery is close to running out of power). Each of these will now be described in greater detail.

Turning first to FIG. 6, a timing diagram between various components of system 60 is shown. These components includes an anchor 116 (that is typically, although not necessarily, included within a headwall unit 68), two pseudo-anchors 118, an access point 170, and an off-product software application 172. Pseudo-anchors 118 and access point 170 are all positioned on patient support apparatus 20. Off-board software 172 refers to software that is positioned off-board patient support apparatus 20, such as software that operates on any one or more one or more electronic devices 110, any one or more servers (e.g. patient support apparatus server 98 and/or server 106c), and/or a combination of one or more of these servers and electronic devices 110. As will be discussed in greater detail below, such software processes data from device 62 and patient support apparatus 20, such as making some or all of it available for display to caregivers, forwarding some or all of it to other servers (e.g. EMR server 106b), and/or performing other actions.

Access point 170 refers to an electronic device that is responsible for forwarding data from device 62 to the off-board software application. In many embodiments, access point 170 corresponds to network transceiver 94. However, this may be varied. For example, in some embodiments, access point 170 may refer to a network transceiver positioned onboard headwall unit 68, in which case data from device 62 is first forwarded to headwall unit 68 before being forwarded to software application 172. Still other configurations are possible.

Location engine 132 is initially set up by anchor 116 sending out relative position messages 174 to pseudo-anchors 118. One of pseudo-anchors 118 is designated a primary pseudo-anchor 118a while the other pseudo-anchor 118 is designated a secondary pseudo-anchors 118b. If location engine 132 is defined by more than two pseudo-anchors 118 onboard patient support apparatus 20, then there will be one primary pseudo-anchor 118a and multiple secondary pseudo-anchors 118b onboard patient support apparatus 20. The primary pseudo-anchor is the pseudo-anchor 118 that receives and processes the relative location estimates of the other pseudo-anchors 118 onboard patient support apparatus 20, as will be explained in more detail below.

Location messages 174 are repetitively sent by anchor 116 (e.g. once every few seconds, although other frequencies may be used). In some embodiments, each message 174 may be sent in a single transmission from anchor 116 to a corresponding pseudo-anchor 118. In other embodiments, location messages 174 are considered to be "sent" only if multiple transmissions are exchanged between anchor 116 and a pseudo-anchor 118. For example, in some embodiments, a message 174 involves an initial transmission from anchor 116 to a pseudo-anchor 118, a response by the pseudo-anchor 118 (and in some embodiments, a further reply by the anchor 116 to the response from pseudo-anchor 118). Still other exchanges may be required before a message 174 is considered to be successfully transmitted.

Message 174, whether conveyed in a single transmission or multiple transmissions, informs the recipient secondary pseudo-anchor 118*b* of its relative position with respect to anchor 116. Thus, when anchor 116 sends a message 174 to secondary pseudo-anchor 118*b*, secondary pseudo-anchor 118*b* is informed of its current relative position with respect to anchor 116. In some embodiments, the relative position is merely a distance. In other embodiments, the relative position includes not only the current distance between secondary pseudo-anchor 118*b* and anchor 116, but also angular information (e.g. Angle of Arrival info) regarding the relative angular relationship of pseudo-anchor 118*b* and anchor 116. As shown in FIG. 6, anchor 116 also sends a message 174 to primary pseudo-anchor 118*a* that informs primary pseudo-anchor 118*a* of its current relative position with respect to anchor 116. In some embodiments, separate messages 174 are sent to each of the pseudo-anchors 118, while in other embodiments, a single message 174 is sent that is received by all of the pseudo-anchors 118 (provided they are within range). In some embodiments where only a single message is sent, location engine 132 may be configured to determine the relative positions of pseudo-anchors 118 (with respect to anchor 116) using Time Difference of Arrival (TDoA) techniques, while in those embodiments where separate messages are sent between anchor 116 and each pseudo-anchor 118, location engine 132 may be configured to determine the relative positions of pseudo-anchors 118 (with respect to anchor 116) using two-way ranging.

After all of the pseudo-anchors 118 onboard patient support apparatus 20 have received message 174, each pseudo-anchor 118 is informed by message 174 of its current relative position with respect to anchor 116. All of the secondary pseudo-anchors 118*b* onboard patient support apparatus 20 then forward their current relative position information with respect to anchor 116 to primary pseudo-anchor 118*a* in a message 176 (FIG. 6). In some embodiments, each pseudo-anchor 118 is communicatively coupled via a wired connection to all of the other pseudo-anchors 118 onboard patient support apparatus 20 (or at least to primary pseudo-anchor 118*a*), and message 176 is sent over this wired connection. In other embodiments, pseudo-anchors 118 may communicate with each other using wireless transmissions, in which case message(s) 176 are sent to primary pseudo-anchor 118*a* wirelessly.

After all messages 176 are received by primary pseudo-anchor 118*a*, primary pseudo-anchor 118*a* is informed not only of its current relative position with respect to anchor 116, but also the current relative positions of the secondary pseudo-anchor(s) 118*b* with respect to anchor 116. In addition, primary pseudo-anchor 118*a* has access to pseudo-anchor location data identifying where each pseudo-anchor 118 is located onboard patient support apparatus 20. This pseudo-anchor location data identifies the relative position of each pseudo-anchor 118 onboard patient support apparatus 20. In some embodiments, this pseudo-location data is specified in the form of a coordinate frame of reference that is fixed with respect to the body of patient support apparatus. In such embodiments, the coordinate location of each pseudo-anchor 118 in this frame of reference is stored in a memory (e.g. memory 140) onboard patient support apparatus 20, and primary pseudo-anchor 118*a* is configured to have access to this pseudo-anchor location data.

Primary pseudo-anchor 118*a* uses this pseudo-anchor location data, along with the relative location data it receives from messages 174 and 176, to determine whether patient support apparatus 20 is positioned within a predefined area of the healthcare facility, such as a bay of a room. This occurs at step 178 (FIG. 7). In general, the predefined areas correspond to areas within several feet of the headwall unit 68 in which the anchor 116 is positioned. If primary pseudo-anchor 118*a* determines that patient support apparatus 20 is positioned within one of these areas, it sends a message 180 (FIG. 6) to access point 170 indicating that patient support apparatus 20 is positioned within one of these predefined areas. The message 180 also includes a unique identification of the predefined area. The unique identification is derived from the device ID 162 that the headwall unit 68 forwards to patient support apparatus 20 (through anchor-to-pseudo-anchor communication and/or through one or both of transceivers 120, 122 transmitting ID 162 to transceivers 134, 136 of patient support apparatus 20). Thus, at step 178, primary pseudo-anchor 118*a* is able to not only determine if it is positioned within a particular predefined area of the healthcare facility, but also what specific area that is (e.g. the room and/or bed of a particular room).

If primary pseudo-anchor 118*a* determines that patient support apparatus 20 is not positioned within a predefined area at step 178, it does not proceeds to send message 180 to access point 170. Instead, location engine 132 continues to repetitively send the messages 174 and 176, and re-perform step 178. If the re-performances of step 178 do not lead to the conclusion that patient support apparatus 20 is positioned in a predefined area, no message 180 is sent, and this looping continues. If any of the re-performances of step 178 do lead to the conclusion that patient support apparatus 20 is positioned within a predefined area, message 180 is sent. In either case, the steps of loop 182 (FIG. 9) continue. In other words, loop 182 continues whether message 180 is sent or not.

If/when message 180 is sent by primary pseudo-anchor 118*a* to access point 170, access point 170 commences executing process 184 (FIG. 6). In process 184, bidirectional communication is carried out between anchor 116 and access point 170. As was noted previously, access point 170 may correspond to network transceiver 94 or, in some embodiments, one of pseudo-anchors 118 (if the pseudo-anchor is configured with network communication abilities that enable it to communicate with network 92). The bidirectional communication between access point 170 and anchor 116 is initiated by access point 170 sending a message 190 to anchor 116 in response to the receipt of message 180.

In some embodiments, the bidirectional communication of process 184 (and 186 discussed below) is carried out by a direct connection between access point 170 and anchor 116, such as, for example, when access point 170 is a WiFi transceiver and anchor 116 (or its associated headwall unit 68) includes a WiFi transceiver. In other embodiments, access point 170 communicates with anchor 116 through one or more of transceivers 134 and 136. In still other embodiments, access point 170 may communicate with anchor 116 using one or more of the pseudo-anchors 118.

Regardless of the communication path between anchor 116 and access point 170, access point 170 sends message 190 to anchor 116 that requests that a data connection be set up between anchor 116 and access point 170 (FIG. 6). Anchor 116 replies with an acceptance of this request via message 192. After receiving acceptance message 192, access point 170 sends a new data connection message 194 to off-product software application 172. Message 194 informs the off-product software application 172 that patient support apparatus 20 is now in communication with a specific anchor 116 (identified by device ID 162, which may be sent in any/all of the messages originating from anchor 116). In some embodiments, message 194 includes the specific ID 162 of anchor 116 and the off-product software application 172 is configured to correlate that specific ID 162 to a specific room number and/or bay number within the healthcare facility, thereby enabling the software application 172 to display the room number/bay area in which patient support apparatus 20 is currently positioned.

After a data connection between anchor 116 and access point 170 has been established via process 184, anchor 116 and access point 170 execute process 186. During process 186, anchor 116 is able to forward data via one or more messages 196 to access point 170, and access point 170 is able to forward data to anchor 116 via one or more messages 198. The data forwarded to access point 170 from anchor 116 may include, in addition to location information, status data about anchor 116, including status data regarding the headwall unit 68 into which anchor 116 is incorporated. Such status data includes, but is not limited to, battery level data (regarding a battery for anchor 116 and/or headwall unit 68), data regarding headwall unit 68's current configuration, data indicating whether headwall unit 68 is currently coupled to nurse call system 82, data indicating whether IR transceiver 122 is able to communicate with IR transceiver 136 aboard patient support apparatus 20, and/or other data.

In some embodiments, headwall units 68 are configured in any of the same manners as the headwall modules 144, 144a disclosed in commonly assigned U.S. patent application Ser. No. 63/26,937 filed May 19, 2020, by inventors Alexander Bodurka et al. and entitled PATIENT SUPPORT APPARATUSES WITH HEADWALL COMMUNICA-TION, the complete disclosure of which is incorporated herein by reference. In such embodiments, the status data sent in one or more messages 196 from anchor 116 to access point 170 may include any of the configuration data of the headwall modules 144, 144a disclosed in this '937 patent application. Headwall units 68 may also or alternatively be configured to operate with any of the same manners as the headwall modules 94 disclosed in commonly assigned U.S. patent application Ser. No. 62/896,075 filed Sep. 5, 2019, by inventors Alexander Bodurka et al. and entitled PATIENT SUPPORT APPARATUSES WITH NURSE CALL CON-NECTION DETECTION, the complete disclosure of which is incorporated herein by reference. In such embodiments, the status data send in one or more messages 196 from anchor 116 to access point 170 may include any of the nurse call connection data, and/or other data, that the headwall modules 94 of the '075 application are configured to detect. Headwall modules 68 may send still other information to access point 170 in one or more messages 196.

The data sent from access point 170 to anchor 116 in one or more messages 198 (FIG. 6) may include commands for taking a variety of different actions. In some embodiments, the commands sent in messages 198 include a command to change the internal configuration of headwall unit 68 so that headwall unit 68 is properly configured to communicate with the particular brand/type of nurse call system 82 that is installed in a particular healthcare facility. The configuration commands may also specify configurations necessary for the headwall unit 68 to communicate with the room's TV 84, room light 86, reading light 88, and/or the particular patient support apparatus 20 assigned to that room (or bed bay).

Software updates may also be communicated to anchor 116 and/or its associated headwall unit 68 via one or more messages 198.

Any of the data received by access point 170 from anchor 116 in one or more messages 196 may be forwarded by access point 170 to off-board software application 172 in one or more messages 206. As was noted, software application 172 may be configured to display some of this data and/or forward it to one or more other servers (e.g. EMR server 106b (FIG. 13)).

The data forwarded from access point 170 to anchor 116 via messages 198 (FIG. 6) may originate from off-product software application 172. In such cases, software application 172 may send one or more messages 204 to access point 170, and some (and/or all) of those messages may contain com-mands, either for access point 170 or for anchor 116. In the latter case, access point 170 forwards the commands to anchor 116 via one or more messages 198.

Anchor 116 is also configured to execute location process 188 (FIG. 6) with primary pseudo-anchor 118a. As will be discussed in greater detail below, process 188 includes anchor 116 sending messages 218 to primary pseudo-anchor 118a whenever anchor 116 detects the presence of a mobile device 62. The term "free node" in FIG. 6 (and other figures) refers to a tagged device 62 that is portable (i.e. freely movable by healthcare personnel). The messages 218 include the relative position of a tagged device 62 as detected by anchor 116. Thus, anchor 116 detects the relative positions of any tagged devices 62 that are positioned within its range and forwards those relative position determinations to primary pseudo-anchor 118a in one or more messages 218. The position of the tagged device 62 with respect to secondary pseudo-anchor(s) 118b is also detected by each such secondary pseudo-anchor 118b. Each secondary pseudo-anchor 118b then forwards that relative position measurement to primary pseudo-anchor 118a in one or more messages 218. And then primary pseudo-anchor 118a deter-mines the position of the device 62 with respect to space volume 64 based upon the content of messages 218, the content of messages 174, 176, and the pseudo-anchor loca-tion data identifying where each pseudo-anchor 118 is located onboard patient support apparatus 20.

It can therefore be seen from FIG. 6, that when patient support apparatus 20 moves within communication range of an anchor 116, it establishes communication with that anchor and, if it is positioned sufficiently close to the anchor, notifies off-board software application 172 of the fact of its close proximity to anchor 116. Further, patient support apparatus 20 automatically establishes communication with anchor 116 in process 184 such that data can be communi-cated in a bidirectional manner between not only anchor 116 and access point 170 during process 186, but also between anchor 116 and off-board software application 172.

In some situations, a patient support apparatus 20 may be moved to a location of the healthcare facility where it is simultaneously in range of multiple anchors 116. In such cases, primary pseudo-anchor 118a will automatically select which one of the multiple anchors, if any, it will set up the communication link of process 184 with. This selection is done during step 178. Specifically, during step 178 the primary pseudo-anchor 118a automatically selects the anchor 116 (if it is in communication with more than one) that is positioned within the predefined area (or "expected location" as stated in FIG. 6). As was noted, the predefined area refers to the area immediately in front of headwall unit 68 where a patient support apparatus 20 is customarily located when it is located in a particular room or bay.

Turning to FIG. 7, it illustrates the operation of location engine 132 when a device 62 ("free node" in FIG. 7) enters the range of location engine 132. As shown therein, location engine 132 executes three different functions: a location determination loop 210, a communication setup process 212, and a data transfer process 214. Turning first to location determination loop 210, device 62 sends location messages 216 to each of the components of location engine 132 (i.e. anchor 116 and all of the pseudo-anchors 118 positioned onboard patient support apparatus 20). Location messages 216, in some embodiments, are the same as messages 174 sent by anchor 116 during loop 182 (FIG. 6) except that they are sent by tag 146 of device 62 instead of anchor 116. Further, just as with messages 174 of loop 182, location messages 216 may comprise only a single transmission or multiple transmissions, as discussed above. Still further, as with messages 174, separate messages 216 may be sent to each recipient, or a single message 216 may be sent that is received by all of the recipients (anchor 116 and pseudo-anchors 118), depending upon the particular technology location engine 132 uses to determine the location of tag 146.

The transmission of location messages 216 (FIG. 7) may be initiated by tag 146 in response to various triggers. In some embodiments, one of anchors 116 and/or pseudo-anchors 118 periodically sends out interrogation messages that prompt tag 146 to respond with messages 216, if it is within range and receiving electrical power. In another embodiment, tag 146 may be configured to automatically send out messages 216 in response to a triggering action that takes place with respect to tag 146, such as, but not limited to, a person turning on electrical power to device 62, taking an action to activate the tag 146 onboard the device 62, and/or undertaking another manual action to prompt tag 146 to start sending out messages 216.

The transmission of location messages 216 to anchor 116 and pseudo-anchors 118 allows each recipient 116, 118 to determine the current relative position of device 62 with respect to itself. Anchor 116 and secondary pseudo-anchor 118b then forward this relative position data to primary pseudo-anchor 118a in messages 218, which are similar to the messages 176 forwarded to primary pseudo-anchor 118a during loop 182 (FIG. 6). Primary pseudo-anchor 118a uses the relative position information from these messages 218, the relative position information it received from tag 146 in message 216, and the pseudo-location data that identifies the relative position of each pseudo-anchor 118 onboard patient support apparatus 20 to determine whether or not tag 146 (and its device 62) are currently positioned inside or outside of space volume 64. If tag 146 is currently positioned inside of space volume 64, primary pseudo-anchor 118a forwards a message 222 to access point 170 and execution of process 212 commences. If tag 146 is not currently positioned inside of space volume 64, primary pseudo-anchor 118a does not forward message 222 to access point 170, execution of process 212 does not commence, and loop 210 continues to repeat.

When access point 170 receives notification that a device 62 is positioned inside of space volume 64 via message 222, it is configured to forward this information to at least one of the following: one or more electronic devices 110, patient support apparatus server 98, and/or another server on network 92. This allows the recipient to share this information with one or more remotely positioned (remote from patient support apparatus 20) caregivers, such as by displaying this information on a display of electronic devices 110 and/or any computers that are in communication with the recipient (or who are the recipient).

After receiving messages 222, access point 170 commences execution of process 212 (FIG. 7) by sending a data connection setup request 224 to the tag 146 of device 62. As with data connection setup request 190 of process 184 (FIG. 6), data connection setup request 224 may include an exchange of credentials, addresses, security information, protocol-information, and/or any other information that is necessary to set up a communication link between tag 146 and access point 170. Tag 146 responds with one or more acceptance messages 226 that contain sufficient data to establish this communication link. In some embodiments, access point 170 may send a message 228 to off-board software application 172 informing it that is has successfully established a communication link with device 62. As with all data forwarded to off-board software application 172, software application 172 may forward this data to one or more additional recipients (e.g. electronic devices 110, etc.).

After the communication link is established between tag 146 and access point 170 during process 212, execution of the bidirectional data transfer process 214 begins. During execution of this process 214, access point 170 is able to send data messages 230 to tag 146 and tag 146 is able to send data messages 232 to access point 170. The content of these messages may vary, depending upon the type of device that device 62 is. In general, the data messages 232 sent from device 62 to access point 170 may include any data that is generated from location module 154 and/or data gathering module 156 of tag 146. Thus, messages 232 may include sensor data from device 62, identification data (e.g. device ID 162), and/or location information from device 62. Any or all of the data received by access point 170 from device 62 in messages 230 may be forwarded in one or more messages 234 to off-board software application 172.

Messages 230 (FIG. 7) from access point 170 to device 62 may include commands, software updates, configuration data, and/or any other information that is desirably communicated to device 62. As with the messages 232, the content of messages 230 may vary for different types of devices 62. Further, the messages 230 sent from access point 170 to device 62 may originate from, or be triggered by, one or more messages 236 that are received from off-board software application 172. In some embodiments, off-board software application 172 is configured to send one or more commands to access point 170 for forwarding to device 62, thereby enabling off-board software application 172 to act as a remote control of one or more aspects of device 62.

FIG. 8 illustrates a state diagram 240 for anchor 116. When anchor 116 is powered on, it starts in a first state 242 where it sends out messages for locating nearby pseudo-anchors 118. Specifically, in first state 242, anchor 116 sends out the messages 174 discussed above with respect to FIG. 6. Anchor 116 moves to a second state 244 when it receives the connection request message 190 (FIG. 6) from primary pseudo-anchor 118a. In second state 244, anchor 116 is able to carry out bidirectional communication with access point 170. That is, in second state 244, anchor 116 is able to carry out any of the communication functions associated with processes 184 or 186. Anchor 116 remains in second state 244 until it receives a disconnection request from access point 170. Such a disconnection request may be sent by access point 170 when primary pseudo-anchor 118a determines at step 178 that it (i.e. patient support apparatus 20) is no longer within the predefined area ("expected location"), which happens when a caregiver moves patient support apparatus 20 to a new location.

Whether in first state 244, anchor 116 is configured to repetitively send out the messages 174 of loop 182 (FIG. 6) to pseudo-anchors 118. Similarly, whether in first state 242 or second state 244, anchor 116 is configured to repetitively send out location messages 218 to primary pseudo-anchor 118*a* whenever it has detected a device 62 positioned within its communication range. Thus, regardless of whether or not anchor 116 has established a bidirectional communication link with access point 170, it is repetitively forwarding location information to pseudo-anchors 118 that indicates their current relative position with respect to anchor 116, as well as repetitively forwarding location information to primary pseudo-anchor 118*a* that indicates device 62's current position relative to anchor 116. This information allows primary pseudo-anchor 118*a* to repetitively not only determine if device 62 is positioned within space volume 62, but also to determine whether patient support apparatus 20 is positioned within a predefined area of the healthcare facility.

FIG. 9 illustrates a state diagram 250 for patient support apparatus 20. Patient support apparatus 20 starts in an initial state 252 where pseudo-anchors 118 are detecting neither the nearby (i.e. within communication range) presence of a device 62 nor the nearby presence of an anchor 116. In this initial state 252, patient support apparatus 20 may be unable to determine its location within the healthcare facility. From initial state 252, patient support apparatus 20 is able to move to either an un-anchored state 254 or an anchored state 256. Patient support apparatus 20 moves to the former when its pseudo-anchors 118 detect a tagged device 62, and it moves to the latter state when its pseudo-anchors 118 detect an anchor 116. When in the unanchored state 254, access point 170 sets up a bidirectional communication link with the tag 146 of the device in a similar manner to the bidirectional communication link that is set up during process 212 (FIG. 7). Thus, access point 170 is able to communicate bidirectionally with tag 146 while in the un-anchored state. The only difference between this communication link and the one set up in process 212 is that access point does not receive any location data (i.e. headwall ID 108) from anchor 116, and therefore is not able to associate the absolute position of patient support apparatus 20 (and device 62) within the healthcare facility.

Regardless of whether patient support apparatus 20 is currently in initial state 252 or un-anchored state 254, it moves to anchored state 256 when pseudo-anchors 118 detect the presence of an anchor 116. When the presence of anchor 116 is detected, primary pseudo-anchor 118*a* determines the absolute position of patient support apparatus 20 within the healthcare facility. When in state 256, patient support apparatus 20 moves to state 258 whenever it detects the presence of a device 62 within space volume 64. In state 258, patient support apparatus 20 (specifically access point 170) carries out the bidirectional communication of processes 212 and 214, including messages to/from off-board software application 172 (e.g. messages 228, 234, and/or 236).

FIG. 10 illustrates a state diagram 260 for a tag 146 coupled to a device 62. Tag 146 may take on two different states: a first state 262 or a second state 264. In the first state 262, tag 146 transmits messages 216 (FIG. 7) to any anchors 116 and/or pseudo-anchors 118 that are within range. In an alternative embodiment, instead of tag 146 transmitting messages 216, anchor 116 and/or pseudo-anchors 118 may transmit messages 216 to tag 146 while it is in first state 262, in which case tag 146 responds to such messages. In first state 262, tag 146 has not established any communication link with any access point 170 onboard any patient support apparatus 20. Tag 146 transitions to second state 264 when it receives a request from an access point 170 to establish such a communication link. This request is sent in message 224 (FIG. 7) from access point 170 to tag 146. In second state 264, tag 146 continues to transmit and/or respond to messages 216, and it also communicates data to and from access point 170. Although not shown in FIG. 10, tag 146 returns back to first 262 whenever it moves outside of space volume 64. More specifically, when tag 146 moves outside of space volume 64, access point 170 sends a notification to tag 146 that it no longer is associated with the particular patient support apparatus 20 (on which access point 170 is located), and that the communication link with access point 170 is being terminated.

FIG. 11 illustrates one example of a software delivery method 270 that may be employed using system 60*m* in order to deliver new software to device 62 and/or its associated tag 146. Software delivery method 270 begins at a step 272 when the off-product software application 172 receives notice that new software is available. In many embodiments, off-product software application 172 is executed, either partially or wholly, on one of the servers of network 92 and it receives notice of such a software update via its connection to the Internet 104. In some embodiments, this software update notification may originate from remote server 100, or another server on the Internet. In any event, regardless of its source, software application 172 receives notification of the availability of new software at step 272.

Prior to, during, or after, this notification, software application 172 sends one or more queries 274 to the access points 170 that it is in communication with. The queries 274 ask each access point 170 for a list of the devices 62 (and their associated tags 146) with which they are currently in communication, as well as the current software version that is implemented on each of these devices 62 and their tags 146. The devices 62 and tags 146 respond to these queries 274 in a series of replies 276, thereby supplying software application 172 with a list of all of the currently connected devices 62 and tags 146.

After receiving the replies 276 (FIG. 11), software application 172 compares the current software versions of the devices 62 to the software version that was identified in the new software notification messages 272 and determines which devices 62 and/or tags 146 do not have the latest software update. After making this determination, software application 172 forwards the list of devices 62 and tags 146 that do not have the latest software to access point 170 in one or more messages 278. Access point 170 informs a healthcare provider of this list in one or more messages 280.

In some embodiments, messages 280 inform the healthcare provider of this list by displaying information on the displays 52 of those patient support apparatuses 20 that have at least one device 62 and tag 146 positioned within their space volume 64 that is in need of a software update. In other words, when an access point 170 receives message 278, controller 138 of patient support apparatus 20 is configured to send a command to one or more of the displays onboard patient support apparatus 20 (e.g. display 52) to display a notification of the availability of a software update.

Alternatively, or additionally, software application 172 may notify healthcare providers of the availability of a new software update by displaying this information on one or more of the electronic devices 110. In such cases, software application 172 forwards this information to the appropriate electronic devices 110. Thus, software application 172 may notify the appropriate healthcare providers of an available software update by causing a notification to be displayed on the displays of those patient support apparatuses 20 that are associated with devices 62 that lack the latest software, by sending messages to the healthcare providers smart phones (e.g. one type of electronic device 110) and/or the communal status monitoring displays (e.g. another type of electronic device 110) that are positioned in various locations within the healthcare facility, or by a combination of both.

Regardless of how the healthcare providers are notified of the availability of a software update for a device 62 and/or tag 146, method 270 is configured to not actually install any software updates without first receiving authorization from a healthcare provider. Thus, method 270 includes a wait-for-authorization step 282. This wait-for-authorization step may be implemented via one or more buttons, switches, or other controls 50 positioned on patient support apparatus 20, and/or one or more buttons, switches, or other controls positioned on one or more of the electronic devices 110. In either case, the healthcare provider indicates his or her assent to begin the actual implementation of the software updates by pressing on the button, switch, or other control. This pressing of the button, switch, or other control results in a message 284 being sent to access point 170 indicating the healthcare provider's assent to commence with the software updating process.

After receiving the authorization message 284 (FIG. 11), access point 170 sends a message 286 to the software application 172 requesting the software update. Software application 172 responds with one or more messages 288 containing the actual software update. After receiving the software update from messages 288, access point 170 forwards the software update to the tag 146 of the device 62 to which the software update applies at step 290. This forwarding takes place over the communication link that is set up as part of process 212 between access point 170 and the device 62.

When tag 146 receives the software update at step 292, it either updates its own software with the new software update (if the update applies to itself), or it communicates the update to device 62 (if the update applies to device 62). In either case, tag 146 and/or device 62 implement the software update at step 292. After completing the software update at step 292, tag 146 sends a software update completion message 294 to access point 170 indicating that the software updating process has been complete. If the software update is not completed, or experiences some other error, tag 146 may send a different notification message to access point 170 indicating that an error occurred during the software updating process. After receiving the software update notification message 294, access point 170 sends one or more messages 296 to software application 172 and/or the healthcare provider indicating that the software update process has been completed. The message 296 to the healthcare provided may be conveyed via one or more messages shown on display 52 of patient support apparatus 20 and/or on the displays of one or more of the electronic devices 110.

FIG. 12 illustrates an end-of-life process 300 that is implemented by system 60 when either a headwall unit 68 and/or a tag 146 (or its associated device 62) approach an end-of-life state. The most common end-of-life state is one in which the battery onboard headwall unit 68 or tag 146 (or device 62) is getting close to being depleted and there is no non-battery source of power available to the headwall unit 68 and/or tag 146 (or device 62). In such cases, the headwall unit 68 and/or tag 146 sends an end-of-life warning message 302 to the access point 170 onboard the associated patient support apparatus 20. Access point 170 responds to messages 302 by sending another end-of-life message 304 to software application 172. Access point 170 may also send an end-of-life message 304a directly to the healthcare provider by displaying a warning, or the like, on one or more of the displays onboard patient support apparatus 20 (e.g. display 52). Software application 172, in response to the receipt of message 304, may notify the healthcare provider of the end-of-life warning by sending another end-of-life message 306 to one or more of the electronic devices 110 that adapted to display the warning on their associated displays (e.g. the caregiver's smart phone, portable laptop computer, and/or a communal display).

The end of life warning messages 302, 304, and 306 are sent when the anchor 116 and/or tag 146 (or device 62) are approaching their end of life, but have not yet reached their end of life. Thus, in some embodiments, messages 302, 304, and 306 are sent when the battery onboard these devices reaches a charge level that is indicative of the need to change and/or re-charge the battery in the near future, but the charge level has not yet reached a depleted level where the anchor 116, and/or tag 146 is going to stop functioning. If/when the anchor 116 and/or tag 146 (or device 62) reach a state where their battery level is going to imminently cause them to stop working, anchor 116 and tag 146 send out the end-of-life messages 308, 310, and 312 (FIG. 11). Messages 308, 310, and 312 are sent in the same manner as messages 302, 304, and 306, but contain a more imminent message that anchor 116 and/or tag 146 are ceasing to function. The messages serve to inform the caregiver that the anchor 116, tag 146, and/or device 62 are no longer functional.

FIG. 13 illustrates a typical layout of system 60 in a manner similar to FIG. 4 but with more detail regarding the servers that are present on local area network 92. As shown in FIG. 13, local area network includes a conventional Admission, Discharge and Tracking (ADT) server 106a, a conventional Electronic Medical Records server 106b, a device/tag server 106c, a conventional nurse call system server 106d, patient support apparatus server 98, and a plurality of conventional wireless access points 96. In some embodiments, the functions of device/tag server 106c and patient support apparatus server 98 are combined into a single server.

ADT server 106a stores patient information, including the identity of patients and the corresponding rooms 66 and/or bays within rooms to which the patients are assigned. That is, ADT server 106a includes a patient-room assignment table 320, or functional equivalent to such a table. The patient-room assignment table 320 correlates rooms, as well as bays within multi-patient rooms, to the names of individual patients within the healthcare facility. The patient's names are entered into the ADT server 106a by one or more healthcare facility staff whenever a patient checks into the healthcare facility and the patient is assigned to a particular room within the healthcare facility. If and/or when a patient is transferred to a different room and/or discharged from the healthcare facility, the staff of the healthcare facility update ADT server 106a. ADT server therefore maintains an up-to-date table 320 that correlates patient names with their assigned rooms.]

EMR server 106b (FIG. 13) stores individual patient records. Such patient records identify a patient by name and the medical information associated with that patient. Such medical information may include all of the medical information generated from the patient's current stay in the healthcare facility as well as medical information from previous visits. EMR table 322 shows an abbreviated example of two types of medical information entries that are commonly found within a patient's medical records: a fall risk entry indicating whether the patient is a fall risk, and a bed sore risk entry indicating whether the patient is at risk for developing bed sores. As noted, EMR server 106b includes far more additional information in the medical records of each patient than what is shown in table 322 of FIG. 13. It will be understood that the term "EMR server," as used herein, also includes Electronic Health Records servers, or EHR servers for short, and that the present disclosure does not distinguish between electronic medical records and electronic health records.

Nurse call server 106d is shown in FIG. 13 to include a caregiver assignment table 324 that matches caregivers to specific rooms and/or bays within the healthcare facility. Although table 324 only shows caregivers assigned to a single room, it will be understood that each caregiver is typically assigned to multiple rooms. In some nurse call systems 82, caregivers are assigned to specific patients, rather than to specific rooms, in which case table 324 may correlate caregivers to individual patients rather than rooms.

Nurse call system server 106d is configured to communicate with caregivers and patients. That is, whenever a patient on a patient support apparatus 20 presses, or otherwise activates, a nurse call (e.g. control 50g, FIG. 3) the nurse call signal is transmitted wirelessly from one or both of transceivers 135, 136 to headwall unit 68, which in turn forwards the signals to communication outlet 76, which in turn forwards the signals to nurse call server 106d via conductors 80 (and/or through other means). The nurse is thereby able to communicate with the patient from a remote location. In some nurse call systems 82, nurse call server 106d is also able to forward alerts and/or other communications to portable wireless devices carried by caregivers and/or to audio stations positioned within patient rooms 66.

Local area network 92 may include additional structures not shown in FIG. 13, such as, but not limited to, one or more conventional work flow servers and/or charting servers that monitor and/or schedule patient-related tasks for particular caregivers, and/or one or more conventional communication servers that forward communications to particular individuals within the healthcare facility, such as via one or more portable devices (smart phones, pagers, beepers, laptops, etc.). The forwarded communications may include data and/or alerts that originate from patient support apparatuses 20 and/or tags 146 (and their associated devices 62).

Device/tag server 106c constructs a table 326 (FIG. 13) that correlates specific devices 62 to specific patient support apparatuses 20. In addition, it correlates both the patient support apparatuses 20 and their devices 62 to specific locations within the healthcare facility. Still further, device/tag server 106c stores data received from devices 62 and correlates this data to the associated patient support apparatus 20 and/or location. In the illustrated embodiment, device/tag server 106c is adapted to execute off-board software application 172, and therefore communicates bidirectionally with the access point 170 of each patient support apparatus 20 in the manners previously described. However, it will be understood that in other embodiments, off-board software application 172 may be executed by a different server (or computer) and device/tag server 106c may be adapted to communicate with that other server/computer in order to receive the data that software application 172 receives from each device 62. In either situation, device/tag server 106c is adapted to communicate with electronic devices 110 via network 92 and its wireless access points 96.

Thus, for example, server 106c is configured to forward data to electronic devices 110 via wireless access points 96 indicating the status of any one or more of the devices 62, thereby allowing caregivers who are not positioned adjacent to patient support apparatus 20 to be remotely apprised of the status of one or more devices 62 that are being used with particular patients within the healthcare facility.

Device/tag server 106c determines the location of each device 62 within the healthcare facility, as well as the patient support apparatus 20 is it associated with, by receiving one or more messages 330 from patient support apparatuses that correlate the unique patient support apparatus ID 58 with the headwall unit IDs 108 and device IDs 162. In other words, when patient support apparatus 20 establishes communication with a headwall unit 68, that headwall unit forwards its headwall ID to patient support apparatus 20 (either via one or both transceivers 120, 122 or via anchor 116). In addition, when a device 62 is positioned within the space volume 64 associated with patient support apparatus 20, that device 62 forwards its unique ID 162 to patient support apparatus 20 (such as via the tag's communication with access point 170 of patient support apparatus 20). The patient support apparatus 20 therefore receives the unique ID of both its adjacent headwall unit 68 and any devices 62 that are positioned within its associated space volume 64. Patient support apparatus then forwards its own ID 58, the device ID(s) 162, and headwall unit 68's ID 108 in one or more messages 330 to network 92.

Messages 330 are directed to patient support apparatus server 98, device/tag server 106c, or both. If directed to only one of these servers, the content of messages 330 may be shared by the recipient server with the other server. In either case, one or both of servers 98 and 106c include a table, or have access to a table, that correlates the unique IDs of each headwall unit 68 with specific locations (rooms and/or bays of rooms) within the healthcare facility. Thus, servers 98 and 106c are able to correlate patient support apparatuses 20 and devices 62 to specific rooms and/or bays of the healthcare facility.

In addition to sending messages 330, patient support apparatuses 20 are further adapted send status data messages 332 to network 92 via network transceiver 94 which, as noted previously, may act as access point 170. As with messages 330, messages 332 may be sent to server 98, server 106c, or both. In some embodiments, message 332 that contain patient support apparatus data are sent to server 98 and messages 332 that contain device 62 data are sent to server 106c. Regardless, as noted before, servers 98 and 106c are in communication with each other and configured to share information between themselves. Indeed, as was also previously noted, servers 98 and 106c may be combined into a single server in some embodiments. The status messages 332 contain data about the status of patient support apparatus 20 and the status of devices 62.

The patient support apparatus status messages 332 may contain any information that is generated by patient support apparatus 20, such as, but not limited to, the status of any of its siderails 36, its brake, the height of litter frame 28, the state of its exit detections system 56, and/or any other data. The device status messages 332 may contain any information about devices 62 that are of interest to remote caregivers, technicians, and/or other personnel. The device status messages 332 include all of the messages labeled with the reference number 234 in FIG. 7. Thus, although FIG. 13 only illustrates messages being sent off of patient support apparatus 20 to network 92, it will be understood that servers 98 and 106c are capable of sending data to patient support apparatus 20, and such communications include the messages 236 discussed above with respect to FIG. 7 that are sent by software application 172 to access point 170.

In some embodiments, servers 98 and 106c are configured to share the patient support apparatus data and device data they receive (via messages 332) with only caregivers who are responsible for the patient associated with the particular patient support apparatus and/or device that the message 332 pertains to. In other words, in some embodiments, servers 98 and 106c are configured to forward data to only a subset of the electronic devices 110, and that subset is chosen based on the caregivers who are responsible for a particular patient. In this manner, for example, a caregiver who is assigned to patients A-G will not receive status messages on his or her associated electronic device 110 (e.g. smart phone) for patient support apparatus and/or device data that pertains to patients H-Z.

Servers 98 and/or 106c may be configured to determine which electronic devices 110 to forward patient support apparatus and device status data to based on information they receive from other servers. Specifically, once servers 98 and/or 106c know the room (and/or bay) that the status data pertains to, they can correlate this room with a particular patient by consulting ADT server 106a and/or nurse call server 106d (or another server on network 92) that correlates rooms to specific caregivers. Once the specific caregiver is identified, servers 98 and/or 106c are further configured to maintain, or have access to, a list that identifies which electronic devices 110 are associated with which caregivers. Messages can then be sent by servers 98 and/or 106 to only the appropriate caregivers.

Figure 14:
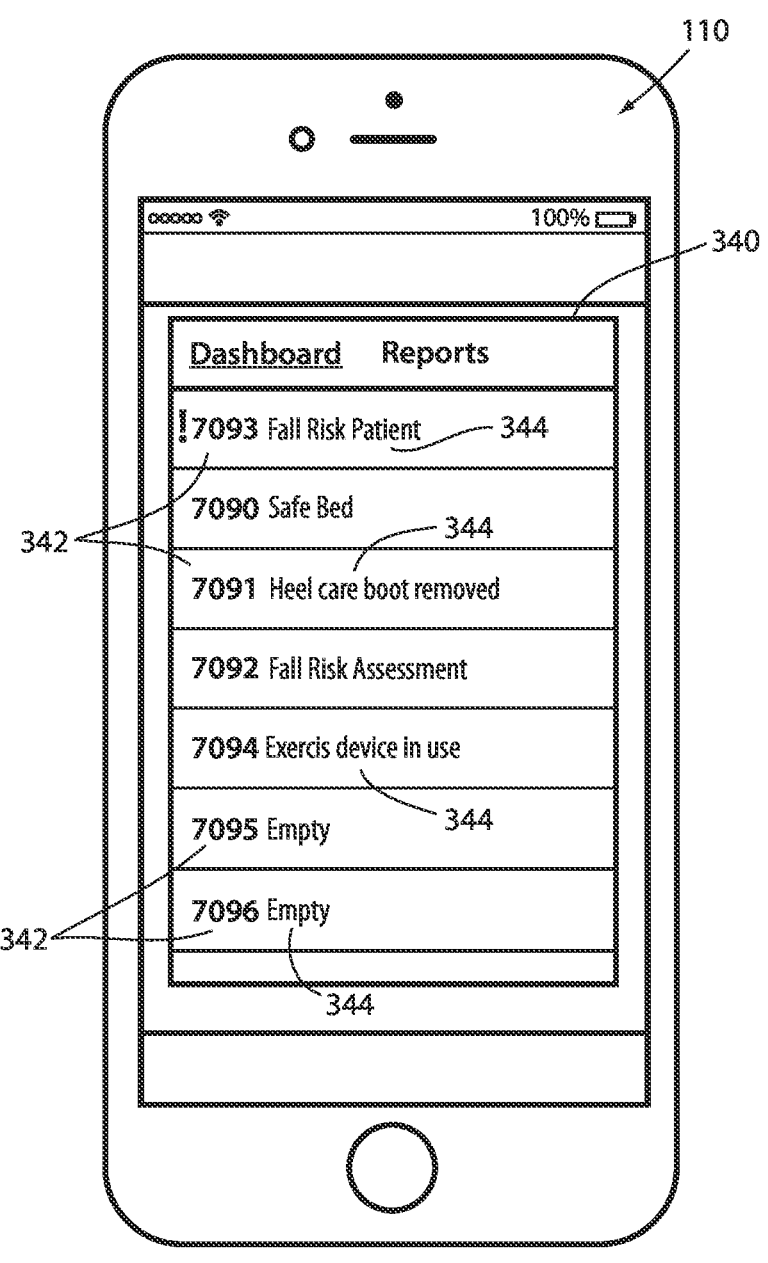
FIG. 14 is a first example of a screen that may be displayed on a remote electronic device that shows the status of multiple patient support apparatuses and devices.

As shown in FIG. 14, some electronic devices, such as electronic device 110a, are communal electronic devices that are intended to be viewed by multiple caregivers, such as all caregivers that are assigned to a particular wing, department, unit, or some other segment of the healthcare facility. When the healthcare facility includes such communal electronic devices 110a, servers 98 and/or 106c are programmed with a table, or programmed to have access to such a table, that lists the rooms that are associated with each such electronic device 110a. Thus, for example, a first communal electronic device 110a may be intended to display data for rooms 400 through 440, while a second communal electronic device 110a may be intended to display data for rooms 450 through 490. In such a case, servers 98 and/or 106c are informed of the room assignments for each electronic device 110a and thus only send status data for a particular room to the electronic device(s) 110a that are intended to display data for that particular room.

Patient support apparatus server 98 constructs a table 328 that correlates individual patient support apparatuses 20 and their current statuses to specific rooms and/or bays within the healthcare facility. As was described previously, in order to construct table 328, server 98 receives the unique patient support apparatus identifiers 58, along with the current status of the patient support apparatuses 20, via messages 330 and 332. Server 98 includes a table (not shown), or has access to a table, that contains the surveying data performed when headwall units 68 were installed within the healthcare facility, and which correlates the specific headwall unit IDs 108 with specific locations within the healthcare facility. This data may be shared with server 106c, or server 106c may have a separate copy of it.

In any of the embodiments disclosed herein, server 106c may be configured to additional execute a caregiver assistance software application of the type described in the following commonly assigned patent applications: U.S. patent application Ser. No. 62/826,097, filed Mar. 29, 2019 by inventors Thomas Durlach et al. and entitled PATIENT CARE SYSTEM; U.S. patent application Ser. No. 16/832, 760 filed Mar. 27, 2020, by inventors Thomas Durlach et al. and entitled PATIENT CARE SYSTEM; and/or PCT patent application serial number PCT/US2020/039587 filed Jun. 25, 2020, by inventors Thomas Durlach et al. and entitled CAREGIVER ASSISTANCE SYSTEM, the complete disclosures of which are all incorporated herein by reference. In still other embodiments, off-board software application 172 may be merged with the caregiver assistance software application described in the aforementioned patent applications such that software application 172 is capable of not only performing the functions described herein, but also any one or more of the functions described in the aforementioned applications.

It will be understood that, although system 60 has been primarily described herein as pertaining to determining the location of one or more tagged devices 62 with respect to a particular patient support apparatus 20, system 60 may be implemented in multiple rooms and/or multiple locations within a healthcare facility for multiple patient support apparatuses 20. Thus, for example, system 60 may include multiple patient support apparatuses 20, multiple space volumes 64 (for each of the rooms, bays, and/or patient support apparatuses), and multiple sets of headwall units 68 and, in some embodiments, multiple anchors 116. System 60 may therefore, at any given time, be monitoring the position of one or more devices 62 with respect to a first volume 64 and a first patient support apparatus 20 while also monitoring the positions of one or more other devices 62 with respect to other patient support apparatuses 20 and their respective space volumes 64.

Although FIG. 4 illustrates an embodiment of system 60 that includes a single anchor 116 integrated into headwall unit 68, and two pseudo-anchors 118 integrated into patient support apparatus 20, it will be understood by those skilled in the art that this arrangement may be varied considerably. Thus, for example, one or more additional pseudo-anchors 118 may be added to patient support apparatus 20 (such as, but not limited to, four pseudo-anchors with one positioned adjacent each corner of patient support apparatus 20). As another example, one or more additional anchors 116 may be added, whether included in headwall unit 68 or configured as stand-alone anchors 116. In general, the components, operation, and layout of system 60 may take on a wide variety of different forms, including, but not limited to, any of the embodiments disclosed in commonly assigned U.S. patent application Ser. No. 63/154,677 filed Feb. 27, 2021, by inventors Celso Pereira et al. and entitled SYSTEM FOR DETERMINING PATIENT SUPPORT APPARATUS AND MEDICAL DEVICE LOCATION, the complete disclosure of which is incorporated herein by reference.

In some embodiments, one or more of the anchors 116, pseudo-anchors 118, and/or tags 146 disclosed herein may use one or more conventional beamforming techniques to narrow the range over which they are able to communicate, thereby allowing a finer granularity in their positions to be determined. Further details of the beamforming techniques that may be implemented into one or more embodiments of system 60 are described in the aforementioned '677 application, which has already been incorporated herein by reference.

In any of the various embodiments of system 60, controller 138 of patient support apparatus 20 may be adapted to generate additional information about the position and orientation of patient support apparatus 20 with respect to headwall unit 68 via its communication with the infrared transceiver 120 of headwall unit 68. That is, the infrared transceiver 120 of headwall unit 68 is configured to only be able to successfully communicate with the infrared transceiver 134 of patient support apparatus 20 if head end 38 of patient support apparatus 20 is positioned generally in front of and facing headwall unit 68. This is because IR transceiver 134 of patient support apparatus 20 is attached to the head end of patient support apparatus 20 and because these IR communications rely on an unobstructed line of sight pathway between headwall unit 68 and patient support apparatus 20. Thus, controller 138 is able to determine from its successful communication with IR transceiver 120 that its head end is oriented toward headwall 74 (to which headwall unit 68 is mounted), and that it is within the relatively short communication range of headwall unit 68 (e.g. on the order of five to ten feet). This position and orientation information may be combined with the position information obtained from the anchors and pseudo-anchors in order to determine the location of a tagged device 62 relative to the space volume 64.

In any of the various embodiments of system 60, controller 138 of patient support apparatus 20 may also be adapted to generate additional information about the position of patient support apparatus 20 and/or device 62 with respect to one or more other patient support apparatuses 20 that have pseudo-anchors 118 that are positioned within communication range. That is, if system 60 determines a location and/or orientation of a first patient support apparatus 20 with respect to a particular room (or other landmark within the healthcare facility), system 60 may have the pseudo-anchors 118 aboard the first patient support apparatus 20 communicate with a tagged device 62 positioned adjacent a second patient support apparatus 20, and/or communicate with one or more pseudo-anchors 118 positioned aboard the second patient support apparatus 20. This communication provides additional estimates of the position of the tagged device 62 and/or second patient support apparatus 20, and therefore may be able to provide a more accurate estimate of the position of the tagged device 62 vis-a-vis its respective space volume 64.

It will be understood by those skilled in the art that any of the different configurations and/or embodiments of system 60 that are described herein may be combined, either wholly or partially, with each other. Some of the combinations may take place throughout an entire healthcare facility, while others of these combinations may take place in only an individual room and/or in other locations. Thus, for example, in some embodiments, some rooms of a particular healthcare facility may include two headwall units 68, while other rooms of the same healthcare facility may include only a single anchor 116. Different patient support apparatuses 20 may also include different numbers and/or positions of pseudo-anchors 118. Still other variations and combinations of any of the features and/or functions of the various embodiments of system 60 may be implemented.

In addition to making status information received from patient support apparatuses 20 via messages 330, 332 available to one or more electronic devices 110, servers 98 and/or 106c are configured, in at least some embodiments, to forward any relevant data that they receive to EMR server 106b for recording in a particular patient's medical record. Thus, data from a tagged device 62 that is positioned within a space volume 64 may have its data automatically transmitted to EMR server 106b, and automatically recorded in the patient assigned to the patient support apparatus 20 about which the space volume 64 is defined. In other words, data from a device 62 is automatically recorded in the electronic medical record of the patient who is positioned in, either partially or wholly, that same space volume 64 as the device, thereby relieving the caregiver from having to take any manual steps to associate the data from that device 62 with that particular patient.

FIG. 14 illustrates one example of an electronic device 110 that may be in communication with servers 98 and/or 106c and display both patient support apparatus status data and device data. In the embodiment shown in FIG. 14, electronic device 110 is a cell phone that executes software that is either part of, or in communication with, software application 172 (which, as noted, is executed on, or as part of, device/tag server 106c). It will, of course, be understood that other types of electronic devices 110 may be part of system 60.

Electronic device 110 of FIG. 14 is shown displaying a multi-room dashboard screen 340. Dashboard screen 340 includes a plurality of individual room numbers 342 and corresponding status messages 344 indicating one or more parameters about the status of the patient assigned to that room (and/or bay of a multi-person room). The parameters that are displayed may refer to parameters that are associated with patient support apparatus 20, parameters that are associated with one or more devices 62 that are positioned within the volume of space 64 associated with a particular patient support apparatus 20, and/or parameters that are associated with a particular patient. Thus, for example, as shown in FIG. 14, status messages 344 may indicate that a patient is a fall risk, that a patient support apparatus 20 is in a "safe bed" configuration, that a heel care boot 62 was removed from a patient in a particular room (e.g. room 7091), that a patient needs to have a fall risk assessment performed, that an exercise device is currently in use in a particular room, that a particular room is empty (no patient), and/or a wide variety of other information. In some embodiments, when a user taps on, or otherwise selects one of the rooms 342 shown on screen 340, the electronic device 110 is configured to display additional information about the room, including more detailed aspects of the patient data, patient support apparatus data, and/or device data.

Figure 15:
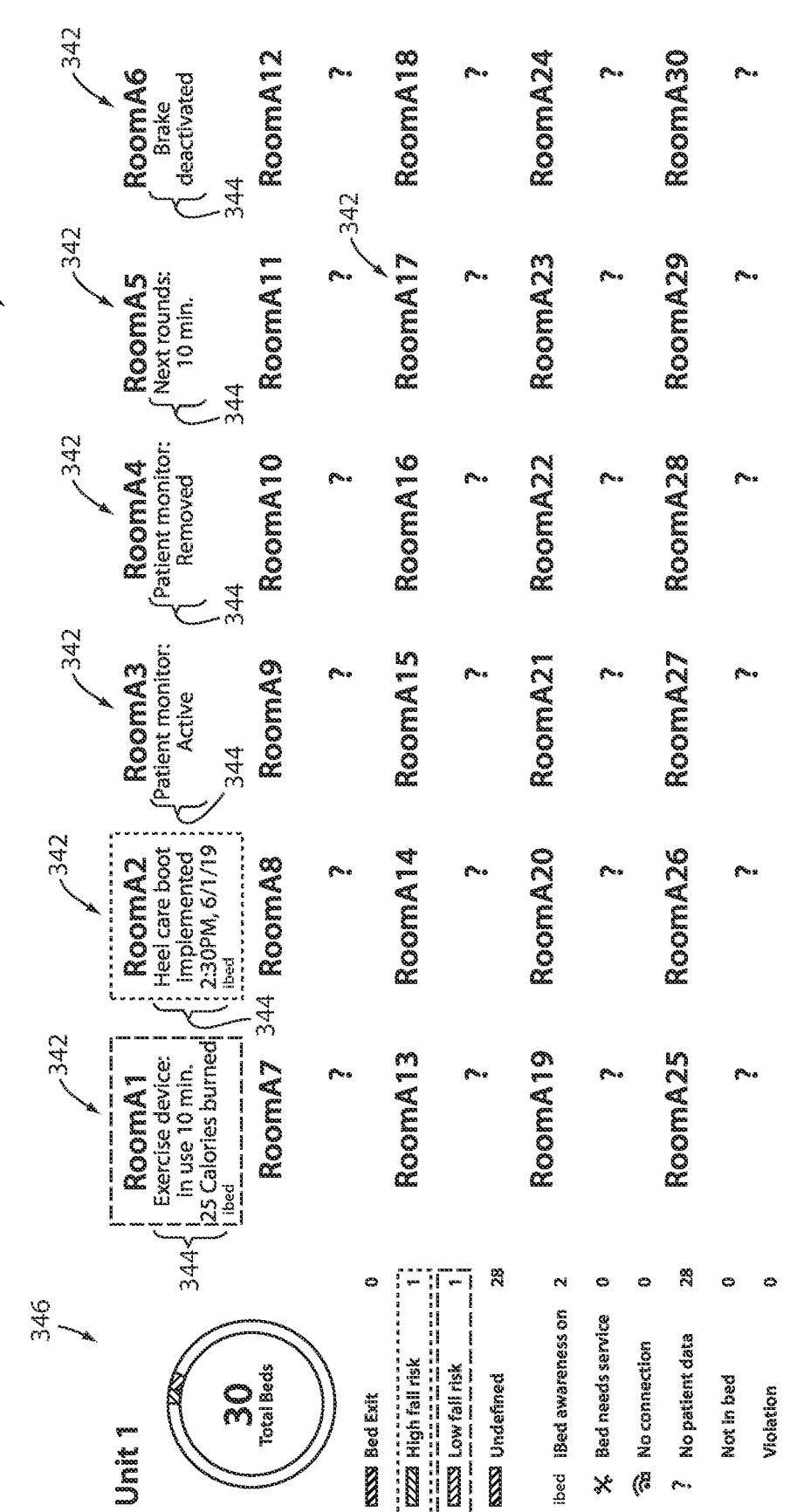
FIG. 15 is a second example of a screen that may be displayed on a remote electronic device that also shows the status of multiple patient support apparatuses and multiple devices.

FIG. 15 illustrates another example of a multi-room dashboard screen 350 that may be displayed on an electronic device 110, such as a communal electronic device 110a (see FIG. 13). Electronic device 110a, in some embodiments, includes a WiFi connection for communicating with an access point 96 of network 92, and thus is able to receive status data from server 98 and/or 106c. Dashboard screen 350, like dashboard screen 340 of FIG. 14, includes a plurality of individual room numbers 342 and corresponding status messages 344 indicating one or more parameters about the status of the patient assigned to that room (and/or bay of a multi-person room). As with screen 340, the parameters that are displayable on screen 350 include parameters that are associated with patient support apparatus 20, parameters that are associated with one or more devices 62 that are positioned within the volume of space 64 associated with a particular patient support apparatus 20, and/or parameters that are associated with a particular patient. Thus, for example, as shown in FIG. 15, status messages 344 may indicate that an exercise device has been in use for ten minutes and the patient has burned 25 calories (room A1), that a heel care boot 62 has been applied to a patient as of 2:30 PM on Jun. 1, 2019 (room A2); that a patient monitor 62 is active (room A3); that a patient monitor has been moved out of proximity with a patient (e.g. out of space volume 64) (room A4); that a caregiver is expected to perform a rounding duty for a patient within a specific time period (room A5); that a brake on patient support apparatus 20 is deactivated (room A6); and/or a wide variety of other types of information.

Screen 350 may also include a summary status area 346 that lists certain collective data statistics about patient support apparatuses 20, devices 62, and/or their associated patients. For example, summary area 346 may indicate how many patient support apparatuses 20 are currently issuing an exit alert (detected by exit detection system 56); how many patients are classified as high or low fall risks (or whose fall risk categorization has not been completed); how many patient support apparatuses 20 have an onboard monitoring system activated; how many patient support apparatuses 20 are in need of service; how many are not connected to network 92, and/or other data. As with screen 340, tapping on any individual room 342 of screen 350 may cause the electronic device 110*a* to display additional information about the status of the patient, patient support apparatus 20, and/or any device(s) 62 that are positioned in that room.

Figure 16:
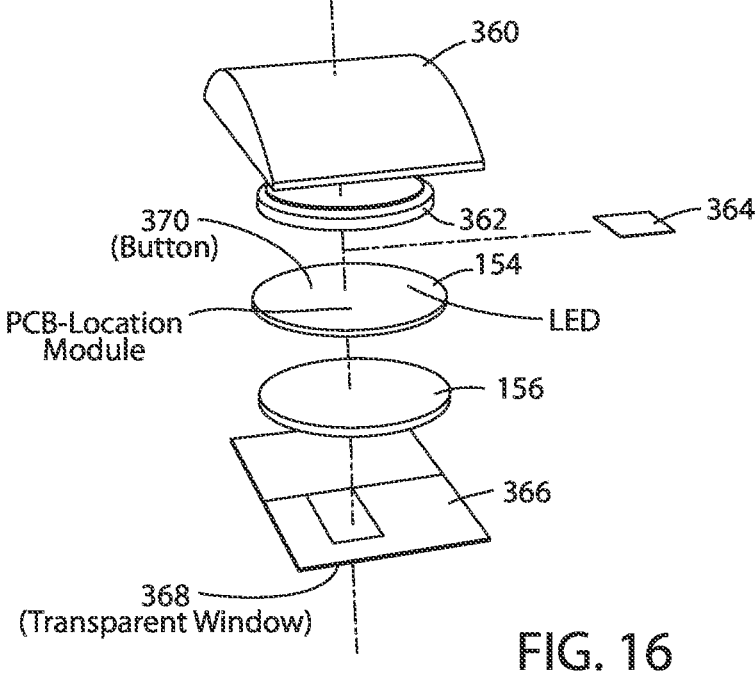
FIG. 16 is an exploded perspective view of one embodiment of an electronic tag that may be used with the devices discussed herein.
Figure 17:
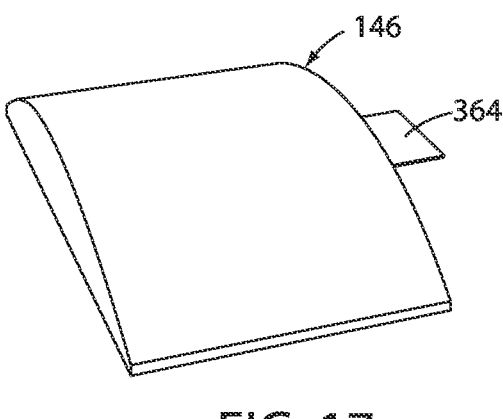
FIG. 17 is a perspective view of the electronic tag of FIG. 16.

FIGS. 16 and 17 illustrate an example of a tag 146 that may be attached to, and/or integrated into, a device 62 in accordance with the disclosure herein. As shown in FIG. 16, tag 146 includes a top cover 360, a battery 362, an activation tab 364, location module 154, data gathering module 156, and a bottom cover 366. In some embodiments, location module 154 includes an activation button 370, or other hardware, that allows a user to manually activate tag 146. Still further, in some embodiments, bottom cover 366 may include a transparent window 368 to enable one or more sensors that are attached to data gathering module 156 to sense one or more visibly-detectable parameters outside of tag 146 (e.g. light readings, camera images, etc.). In some embodiments, transparent window 368 may include one or more openings for sensors to come in physical contact with the patient, a portion of device 62, and/or other structures.

In some embodiments, activation tab 364 is a pull tab having a body sufficiently long to provide a temporary electrical insulation barrier between one or more the batteries 362 positioned within tag 146 and the electronic circuitry that draws power from the battery(ies) 362. Thus, when pull tab 364 is in the position shown in FIG. 16 the battery or batteries are prevented from supplying electrical power to the electronic components within tag 164, thereby preserving the life of the battery. When device 62 is to be used with a particular patient, the caregiver (or other authorized user) pulls activation tab 364 until it is removed from tag 164, or is otherwise sufficiently moved to remove the electrical barrier between battery 362 and the electronic components of (e.g. modules 154, 156 of tag 146).

In some embodiments, tag 146 is configured to automatically start communicating with any in-range pseudo-anchors 118 and/or anchors 116 automatically upon receipt of power from battery 362 (which supplies electrical power to both modules 154 and 156). Thus, in some embodiments, when a user pulls on activation tab 364, the electronics of tag 164 immediately begin operating to carry out the functions described herein, and there is no need for the user to take any additional steps. It will, of course, be understood that, either in lieu of, or in addition to, activation tab 364, tag 146 may include one or more buttons, such as button 370, or another type of control, that must be manually activated by a user in order for tag 146 to begin communicating with an in-range location engine 132.

In the illustrated embodiment, tag 146 is constructed such that the electronics of location module 154 are mounted to a printed circuit board (PCB) that is separate from a PCB board to which the electronics of data gathering module 156 are mounted. This construction is selected so that tag 146 may be more easily customized to different devices. That is, for each type of device 62 to which tag 146 may be coupled, location module 154 may be the same, but data gathering module 156 may be different. This is because different types of devices will include different types of sensors, and those sensors are mounted to, or connected to, data gathering module 156. Thus, by including a separate location module 154 that is the same for all devices 62, it is easier to customize tag 146 to a particular device 62 by simply replacing data gathering module 156 with a module 156 that is specific to that particular device 62. In other words, rather than having to redesign all of tag 146 for use with different devices 62, it can be re-designed for different devices by simply replacing data gathering module 156 and leaving all of the other components unchanged. Other constructions of tag 146 may, of course, be utilized.

The sensors that may be part of data gathering module 156 can vary widely. In some embodiments, the sensors of data gathering module 156 may include one or more of the following: accelerometers, magnetometers, gyroscopes, humidity sensors, altitude sensors, temperature sensors, air flow sensors, load cells, strain gauges, etc. The outputs of these sensors are processed by circuitry onboard data gather module 156 and forwarded to location module 154. Location module 154 then communicates this data to access point 170 when tag 146 is positioned within a space volume 64, as was discussed above.

In some embodiments, in order to extend the life of a battery, tag 146 may include circuitry to automatically enter a reduced power mode after a certain amount of time of non-use of the associated device 62. Once such a power-saving mode has been entered, tag 146 may wait for a user to manually press a button (e.g. button 370), or to take some other physical action, to cause tag 146 to exit the power-saving mode and return to its normal operating mode. In other embodiments, tag 146 may be configured to automatically exit the power-saving mode upon detecting activity from one or more of the sensors of data gathering module 156 that are indicative of device 62 resuming active operation. Still other manners for conserving the battery life may be utilized.

Battery 362, in at least some embodiments, is a rechargeable battery. Further, in some embodiments, tag 146 may be constructed such that top cover is easily removed from the rest of tag 146 such that battery 362 may be easily replaced when it has been drained. Still further, in some embodiments, circuitry may be included within tag that allows battery 362 to be wirelessly re-charged without requiring any disassembly of tag 146.

Bottom cover 366, in some embodiments, may include an adhesive, one or more hooks, fastening straps, and/or other structures that are used to secure tag 146 to device 62, to the extent tag 146 is not built into device 62. Location module 154, in addition to containing the circuitry used for determining location, may include additional components, such as one or more status LEDs, or other status indicators, a power on/off switch or button (either in lieu of, or in addition to, activation tag 364), a pairing control switch or button (used, for example, to manually pair tag 146 with an electronic device 110 via data transceiver 152 (FIG. 5)), and/or other components.

In some embodiments, device 62 may be a badge adapted to be worn by caregivers and/or other individuals. In such embodiments, the caregiver badge may be a badge of the type sold or marketed by Stryker Corporation of Kalamazoo, Michigan, under the names Vocera badge, Vocera smart badge, and/or Vocera minibadge. Other types of badges may also, or alternatively, be used. Such caregiver badges 62 include the ability transmit caregiver voice communications to other badges and/or other locations within a healthcare facility. Some of the badges may also include text messaging abilities, alarm notifications, and other functions. When integrated into system 60, such badges 62 are modified to include one or more ultra-wideband pseudo-anchors and/or tags that communicate with pseudo-anchors 118 onboard patient support apparatus 20. That is, patient support apparatus 20 may be configured to repetitively determine the location of any caregiver-worn badges 62 that are positioned within range of its pseudo-anchors 118 and determine whether the badge 62 is positioned inside or outside of volume of space 64.

If the badge 62 (which is worn by a caregiver) moves within the predetermined volume of space 64 (which may have the same dimensions, or different dimensions, than the volume of space 64 used with any one or more of the other devices 62), controller 138 of patient support apparatus 20 may be configured to take one or more automatic actions in response thereto. Such automatic actions include any one or more following: automatically unlocking one or more functions of patient support apparatus 20 that were locked out before the badge 62 moved within volume of space 64; automatically locking one or more functions of patient support apparatus 20 after badge 62 is moved outside of volume of space 64; automatically silencing any alarms that are issuing when badge 62 is moved inside volume of space 64; automatically unsilencing any unresolved alarms that exist when badge 62 is moved outside of volume of space; automatically preventing lifts 26 from raising litter frame 28 above a threshold height if badge 62 is moved outside of volume of space 64; automatically enabling lifts 26 to raise litter frame 28 above the threshold height if badge 62 is moved inside of volume of space 64; automatically turning on one or more lights (e.g. room light 86 or reading light 88) and/or automatically turning off (or muting) television 84 when the badge 62 is moved inside of space volume 64; automatically turning off one or more lights (e.g. room light 86 or reading light 88) and/or automatically turning back on (or unmuting) television 84 when the badge 62 is moved outside of space volume 64; automatically starting and/or stopping a timer when badge 62 is moved inside or outside of volume of space 64 in order to keep track of how much time the caregiver spends with the patient and/or away from the patient; automatically recording a time at which badge 62 is moved inside or outside of volume of space 64 in order to keep track of when the caregiver visited the patient; automatically recording what controls 50 the caregiver presses, or otherwise activates, while the badge 62 is inside space volume 64; and/or performing other automated functions.

Controller 138 of patient support apparatus 20 may be configured to perform any of these automated tasks by itself, or, in some embodiments, it may perform these tasks in cooperation with patient support apparatus server 98 and/or remote server 100. When performing any one or more of these automated tasks that track the positon of the badge 62, controller 138 may be configured to use volumes of space 64 whose dimensions may vary depending upon which particular automated task controller 138 is performing. For example, when automatically silencing an alarm based on the presence of a caregiver badge, controller 138 may use a volume of space 64 that is large enough to encompass substantially all of the room in which patient support apparatus 20 is positioned. In that manner, the alarm may be automatically silenced essentially upon the entry of the caregiver into the room. However, when automatically unlocking a function of patient support apparatus 20, controller 138 may use a smaller volume of space 64 that only encompasses the area immediately surrounding patient support apparatus 20 in which the caregiver would be expected to be positioned if he/she were to manipulate any of the controls 50 onboard patient support apparatus 20. In this manner, controller 138 may automatically silence one or more alarms when the caregiver wearing a badge 62 enters a room, but wait to unlock one or more functions of patient support apparatus 20 until the caregiver has arrived at the patient support apparatus 20. The different volumes of space may be defined within memory 140 and controller 138 may automatically select which definition to use based on the particular automated function it has been configured to implement.

Controller 138 and/or server 98 are further configured, in some embodiments, to utilize the tracking of caregiver badges 62 inside and outside of volumes of space 64 in order to provide automatic protocol reminders to caregivers, to provide automatic charting or verification of rounding tasks, and/or to provide automatic rounding reminders. Each of these functions will now be described in more detail.

With respect to automatic protocol reminders, controller 138 and/or server 98 may be configured to monitor how often a caregiver with a badge 62 attends to a patient while he or she is supported on patient support apparatus 20 (using the communications previously described between pseudo-anchors 118 and the UWB transceiver coupled the caregiver's badge 62). Controller 138 and/or server 98 may also have criteria stored in a memory accessible to either of them that defines one or more protocols that are to be implemented with the patient. Such protocols may involve turning the patient at certain intervals, applying therapies to the patient at certain times and/or at certain intervals, moving the patient out of patient support apparatus 20 at certain intervals or times, etc. Controller 138 and/or server 98 may be configured to monitor badge 62's movement inside and outside of volume of space 64 to determine whether one or more of these protocols are being met in a timely fashion and/or at the specified intervals. In some instances, where the protocol requires certain actions to be taken on the patient support apparatus (e.g. move litter frame 28 to a low height, implement a therapy using mattress 42, etc.), controller 138 may, in addition to monitoring the presence of the badge 62 within space volume 64, monitor which controls 50 are activated by the caregiver to determine whether the specified protocol was performed or not.

If controller 138 determines that a protocol was not properly followed, it may issue an alert via one or more of the control panels 54 and/or send a message to server 98. Server 98 may be configured to forward this alert to the electronic device 110 associated with the caregiver for that particular patient, to the electronic device 110 associated with the caregiver's manager, and/or to other personnel. If controller 138 determines that a protocol was properly followed, controller 138 may send a message to server 98 indicating that the protocol was properly implemented, and server 98 may forward messages reflecting this fact to one or more electronic devices 110. Alternatively, or additionally, server 98 may automatically forward the successful completion of a protocol, or step or steps of a protocol, to an EMR server on network 92.

Controller 138 and/or server 98 may also be configured to utilize the movement of badges 62 inside and outside of space volume 64 to perform the automatic charting of rounding tasks and/or the automatic issuance of rounding reminders. Typically, healthcare facilities require their caregivers to visit their patients at certain minimum time intervals. These visits are often called rounding. Controller 138 and/or server 98 may be configured, in some embodiments, to consult a memory accessible to either or both of them that defines the healthcare facility's rounding criteria (e.g. time intervals, length of patient visit, etc.), and to automatically determine whether those criteria are being fulfilled or not based on the movement of badges 62 inside and outside of space volume 64. For example, if a caregiver doesn't visit a patient at the required intervals (as determined from the absence of his or her badge 62 within space volume 64 for longer than the required interval), controller 138 and/or server 98 may issue a rounding alert. The rounding alert may be implemented in any of the same manners as the protocol violation alert discussed above.

In addition, controller 138 and/or server 98 may be configured to automatically send reminders to the electronic device 110 associated with a particular caregiver, wherein the reminders indicate to the caregiver which patients he or she needs to visit as part of his or her rounding duties, and/or how much time is left to complete those rounding duties. Still further, when controller 138 and/or server 98 determine that a caregiver has successfully performed a rounding task (as determined by the presence of the caregiver's badge 62 within volume of space 64 for a specified amount of time), server 98 may be configured to automatically enter this data into the patient's electronic medical record (via one or more messages sent to an EMR server). In some of these embodiments, controller 138 and/or server 98 may automatically record the amount of time that the caregiver's badge 62 remains inside volume of space 64 in order to determine how much time the caregiver spent with the patient. This information may be recorded in the patient's EMR, within memory 140 onboard patient support apparatus 20, within a memory accessible to server 98, and/or sent to one or more electronic devices 110. This data may then be retrieved and/or viewed by authorized personnel.

It will be understood that various modifications can be made to system 60 beyond those explicitly described herein. As one example, additional messages may be sent between pseudo-anchors 118, anchor 116, and/or tags 146 beyond those explicitly described herein in order to authenticate these devices, in order to encode their communications, and/or in order to implement other security features designed to prevent interference and/or unauthorized access to the data communicated between these devices. As another example, headwall units 68 and/or patient support apparatuses 20 maybe modified to omit one or both of their respective IR and/or RF transceivers (120, 122, 134, 136), in which case communications between patient support apparatus 20 and headwall unit 68 may take place solely via the remaining transceivers (e.g. the wireless transceivers of anchor 116 and pseudo-anchors 118).

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A system comprising:
   (i) a patient support apparatus comprising:
      (a) a support surface adapted to support a patient;
      (b) a first pseudo-anchor coupled to a first location on the patient support apparatus;
      (c) a second pseudo-anchor coupled to a second location on the patient support apparatus;
      (d) a memory containing pseudo-anchor location data identifying where the first and second locations are defined on the patient support apparatus;
      (e) a network transceiver adapted to communicate with a computer network of a healthcare facility in which the patient support apparatus is positioned;
      (f) a controller adapted to use wireless communications between the first and second pseudo-anchors and a mobile medical device to determine a first relative position of the mobile medical device with respect to the patient support apparatus; and
   (ii) a tag coupled to the mobile medical device, the tag including a location sensing module adapted to communicate information to the first and second pseudo-anchors, and a data gathering module adapted to wirelessly communicate data regarding the operation of the mobile medical device to at least one of the first or second pseudo-anchors.

2. The system of claim 1 wherein the tag includes a common battery adapted to provide electricity to both the location sensing module and the data gathering module.

3. The system of claim 1 further comprising a server hosted on the computer network and adapted to communicate with a display, wherein the server is adapted to forward to the display both first data regarding the patient support apparatus and second data regarding the mobile medical device, the controller is further adapted to forward the first and second data via the network transceiver to the server, the display includes a network interface adapted to communicate with the server, the display is part of a smart phone, a computer tablet, or a laptop computer, the network transceiver is a first WiFi transceiver, and the network interface is a second WiFi transceiver.

4. The system of claim 1 wherein the tag is further adapted to automatically start communicating with the first and second pseudo-anchors in response to a manually initiated triggering action.

5. The system of claim 1 further comprising a server hosted on the computer network and adapted to communicate with a display, wherein the server is adapted to forward to the display both first data regarding the patient support apparatus and second data regarding the mobile medical device, and wherein the controller is further adapted to determine if the mobile medical device is inside or outside of a volume of space, and to send a message to the server indicating whether the mobile medical device is inside or outside of the volume of space.

6. The system of claim 5 further comprising an anchor affixed at a known location to a wall of the healthcare facility, wherein the anchor is configured to wirelessly communicate with the first and second pseudo-anchors in order to determine relative positions of the first and second pseudo-anchors with respect to the anchor; wherein the controller is further adapted to forward the following to the server via the network transceiver: (1) a first unique identifier associated with the patient support apparatus; (2) a second unique identifier associated with the anchor; and (3) a third unique identifier associated with the mobile medical device; and wherein the server is adapted to determine a room number of a room within the healthcare facility in which the patient support apparatus is located based on the second unique identifier.

7. The system of claim 6 wherein the server is further configured to instruct the display to display the room number along with the first data and the second data; wherein the first data includes at least one of the following: a status of a brake onboard the patient support apparatus; a status of an exit detection system onboard the patient support apparatus; a status of a siderail onboard the patient support apparatus; height information of an adjustable height litter frame of the patient support apparatus; an occupancy status of the patient with respect to the patient support apparatus; or a status of a monitoring system onboard the patient support apparatus adapted to monitor a plurality of conditions of the patient support apparatus; and wherein the second data includes at least one of the following: a battery status of the mobile medical device; a usage metric of the mobile medical device; a type of device the mobile medical device is; whether the mobile medical device is inside or outside of the volume of space; or a time at which the mobile medical device entered or exited the volume of space.

8. The system of claim 6 wherein the controller is further adapted to repetitively update the first relative position of the mobile medical device with respect to the patient support apparatus and to repetitively determine if the mobile medical device is inside or outside of the volume of space based on the repetitively updated first relative position.

9. The system of claim 6 wherein the patient support apparatus further comprises a microphone adapted to convert sound from a patient positioned on the patient support apparatus into audio signals, and a wireless transceiver adapted to forward the audio signals to the anchor for forwarding to a nurse call system coupled to the anchor.

10. The system of claim 1 wherein the location sensing module of the tag is adapted to use ultra-wideband signals to communicate with the first and second pseudo-anchors; and wherein the information communicated to the first and second pseudo-anchors by the location sensing module includes location information enabling the first and second pseudo-anchors to determine relative positions of the tag with respect to the first and second pseudo-anchors.

11. A system comprising:
(i) an anchor affixed at a known location to a wall of a healthcare facility;
(ii) a patient support apparatus comprising:
(a) a support surface adapted to support a patient;
(b) a first pseudo-anchor coupled to a first location on the patient support apparatus, the first pseudo-anchor adapted to wirelessly communicate with the anchor in order to determine a first relative position of the first pseudo-anchor with respect to the anchor;
(c) a second pseudo-anchor coupled to a second location on the patient support apparatus, the second pseudo-anchor adapted to wirelessly communicate with the anchor in order to determine a second relative position of the second pseudo-anchor with respect to the anchor;

(d) a memory containing pseudo-anchor location data identifying where the first and second locations are defined on the patient support apparatus;
(e) a network transceiver adapted to communicate with a computer network of the healthcare facility in which the patient support apparatus is positioned;
(f) a controller adapted to use wireless communication between the first and second pseudo-anchors and a mobile medical device to determine a third relative position of the mobile medical device with respect to the patient support apparatus; and
(iii) a server hosted on the computer network and adapted to communicate with a display, the server further adapted to forward to the display both first data regarding the patient support apparatus and second data regarding the mobile medical device.

12. The system of claim 11 wherein the controller is further adapted to forward the first and second data via the network transceiver to the server, the display includes a network interface adapted to communicate with the server, the display is part of a smart phone, a computer tablet, or a laptop computer, the network transceiver is a first WiFi transceiver, and the network interface is a second WiFi transceiver.

13. The system of claim 12 wherein the first and second pseudo-anchors are adapted to communicate with a tag coupled to the mobile medical device, and wherein the tag includes a location sensing module adapted to communicate information to the first and second pseudo-anchors, and a data gathering module adapted to communicate data regarding the operation of the mobile medical device to at least one of the first or second pseudo-anchors.

14. The system of claim 13 wherein the tag includes a common battery adapted to provide electricity to both the location sensing module and the data sensing module.

15. The system of claim 13 wherein the information communicated to the first and second pseudo-anchors by the location sensing module includes location information enabling the first and second pseudo-anchors to determine relative positions of the tag with respect to the first and second pseudo-anchors.

16. The system of claim 12 wherein the first and second pseudo-anchors are adapted to use one of ultra-wideband signals or Bluetooth Low Energy (BLE) signals to determine the first and second relative positions.

17. The system of claim 11 wherein the controller is further adapted to use the anchor to determine the third relative position of the mobile medical device with respect to the patient support apparatus, to determine if the mobile medical device is inside or outside of a volume of space, to send a message to the server indicating whether the mobile medical device is inside or outside of the volume of space, and to forward the following to the server via the network transceiver: (1) a first unique identifier associated with the patient support apparatus; (2) a second unique identifier associated with the anchor; and (3) a third unique identifier associated with the mobile medical device; and wherein the server is adapted to determine a room number of a room within the healthcare facility in which the patient support apparatus is located based on the second unique identifier.

18. The system of claim 17 wherein the server is further configured to instruct the display to display the room number along with the first data and the second data; and wherein the first data includes at least one of the following: a status of a brake onboard the patient support apparatus; a status of an exit detection system onboard the patient support apparatus; a status of a siderail onboard the patient support apparatus; height information of an adjustable height litter frame of the patient support apparatus; an occupancy status of the patient with respect to the patient support apparatus; or a status of a monitoring system onboard the patient support apparatus adapted to monitor a plurality of conditions of the patient support apparatus; and wherein the second data includes at least one of the following: a battery status of the mobile medical device; a usage metric of the mobile medical device; a type of device the mobile medical device is; whether the mobile medical device is inside or outside of the volume of space; or a time at which the mobile medical device entered or exited the volume of space.

19. The system of claim 17 wherein the controller is further adapted to repetitively update the third relative position of the mobile medical device with respect to the patient support apparatus and to repetitively determine if the mobile medical device is inside or outside of the volume of space based on the repetitively updated third relative position.

20. The system of claim 11 wherein the patient support apparatus further comprises a microphone adapted to convert sound from a patient positioned on the patient support apparatus into audio signals, and a wireless transceiver adapted to forward the audio signals to the anchor for forwarding to a nurse call system coupled to the anchor.

\* \* \* \* \*